US005324327A

United States Patent [19]
Cohen

[11] Patent Number: 5,324,327
[45] Date of Patent: Jun. 28, 1994

[54] LOW THRESHOLD CARDIAC PACING LEAD

[76] Inventor: Donald M. Cohen, 17512 Luther, Irvine, Calif. 92714

[21] Appl. No.: 809,583

[22] Filed: Dec. 17, 1991

[51] Int. Cl.$^5$ ............................................. A61N 1/04
[52] U.S. Cl. ................................. 607/122; 607/126
[58] Field of Search ............... 128/784, 785, 786, 642, 128/419 P

[56] References Cited

U.S. PATENT DOCUMENTS

| | | | |
|---|---|---|---|
| 3,754,555 | 8/1973 | Schmitt | 128/785 |
| 3,974,834 | 8/1976 | Kane | 128/418 |
| 4,214,594 | 7/1980 | Little | 182/786 |
| 4,233,992 | 11/1980 | Bisping | 128/785 |
| 4,402,329 | 9/1983 | Williams | 128/785 |
| 4,640,298 | 2/1987 | Pless et al. | 128/419 P |
| 4,643,201 | 2/1987 | Stokes | 128/786 |
| 4,774,952 | 10/1988 | Smits | 128/419 D |
| 4,815,469 | 3/1989 | Cohen et al. | 128/634 |
| 4,844,099 | 7/1989 | Skalsky et al. | 128/785 |
| 4,991,603 | 2/1991 | Cohen et al. | 128/786 |
| 4,998,975 | 3/1991 | Cohen et al. | 128/419 D |
| 5,144,960 | 9/1992 | Mehra et al. | 128/785 |

OTHER PUBLICATIONS

Cannom, David S., *Implantable Cardioverter Defibrillator: The Promise and Perils of an Evolving Technology*, PACE, vol. 15, (Jan. 1992).
Adler et al., *Chronic Animal Testing of New Cardiac Pacing Electrodes*, PACE, vol. 13, (Dec. 1990, Part II).
Stokes et al., *A New Efficient Nano Tip Lead*, PACE, vol. 13 (Dec. 1990, Part II).
Mond et al., *The Electrode-Tissue Interface: The Revolutionary Role of Steroid Elution*, PACE, vol. 15, (Jan. 1992).
Schaldach et al., *Sputter-Deposited TiN Electrode Coatings for Superior Sensing and Pacing Performance*, PACE, vol. 13, (Dec. 1990, Part II).
One page advertisement for a Steroid eluting, platinized pacing lead, *Medtronic*, (Oct. 1991).

Primary Examiner—William E. Kamm
Assistant Examiner—Scott M. Getzow
Attorney, Agent, or Firm—Fitch, Even, Tabin & Flannery

[57] ABSTRACT

An improved implantable pacer lead separates the pacing function and sensing function to the benefit of both pacing threshold and sensing effectiveness. Such separation permits the reduction of the size of the necrotic capsule that forms around the pacing electrode and also permits the use of smaller pacing electrodes which stimulate smaller regions, and therefore require less energy. The separation also permits the use of materials that concentrate the pacing energy where it is needed. The separation further works to the benefit of the sensing function because the sensing electrode may be placed exactly where it is most effective, independent of the optimal pacing electrode position. Similarly the size, shape, material and surface characteristics of the sensing electrode may be optimized irrespective of the pacing electrode.

12 Claims, 13 Drawing Sheets

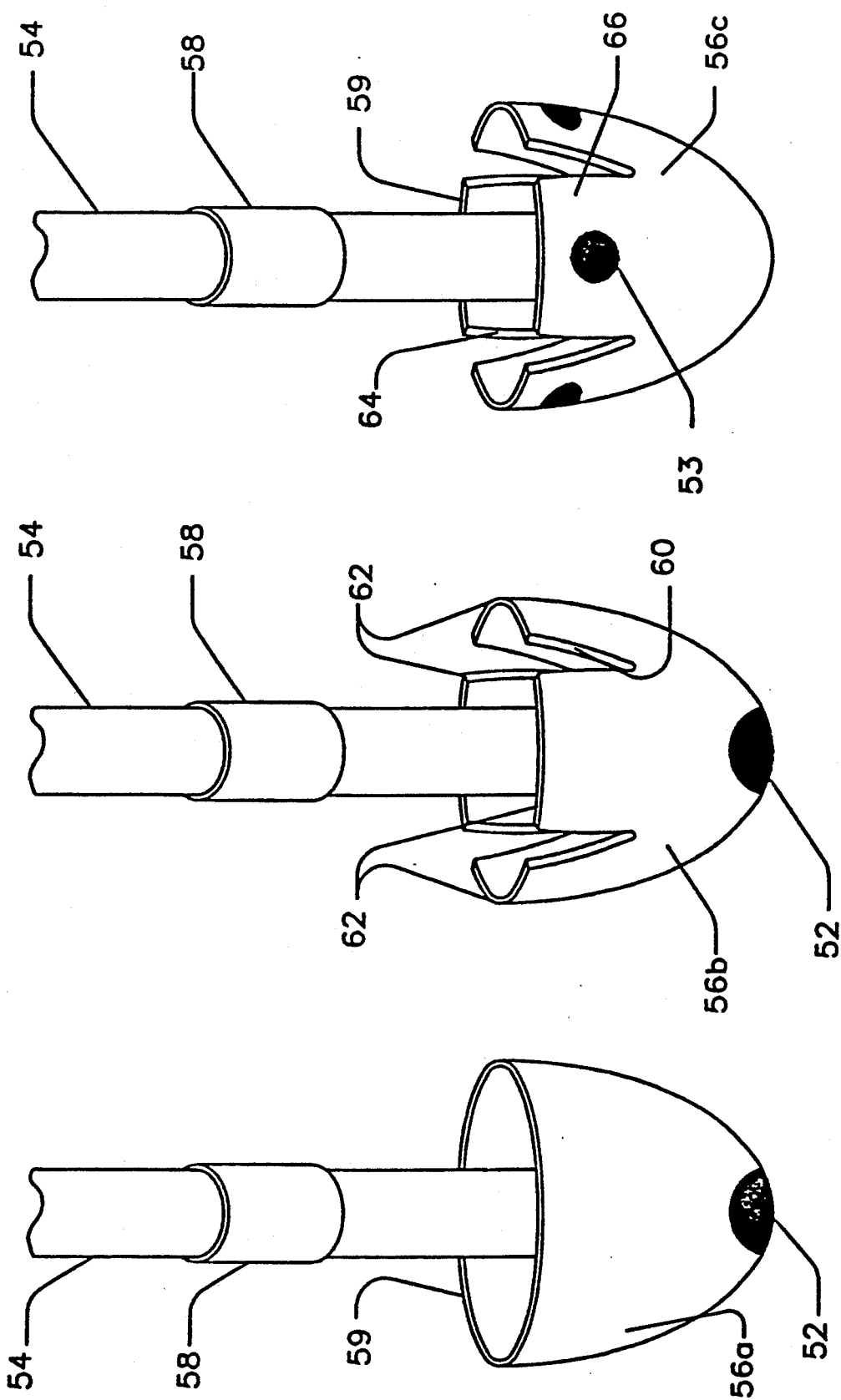

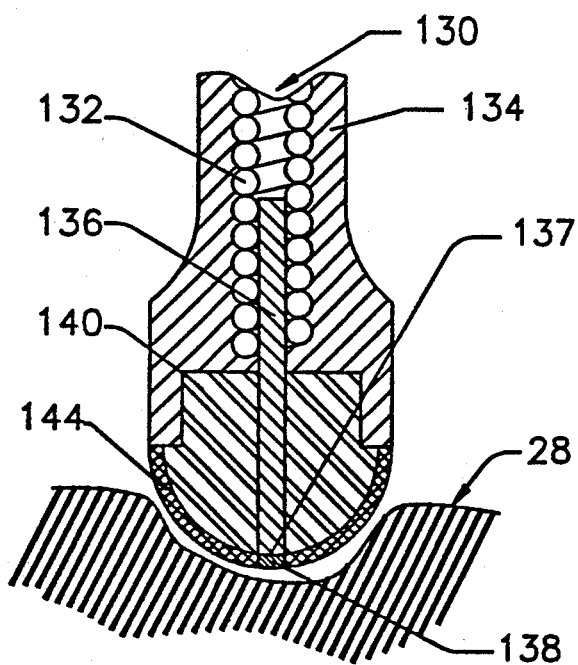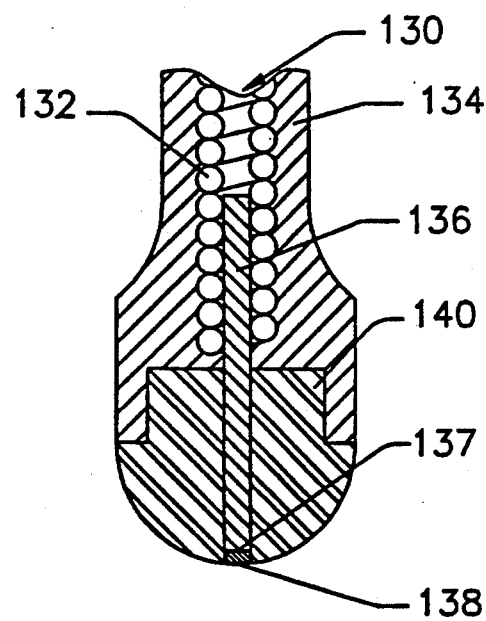
FIG. 15A
FIG. 15B
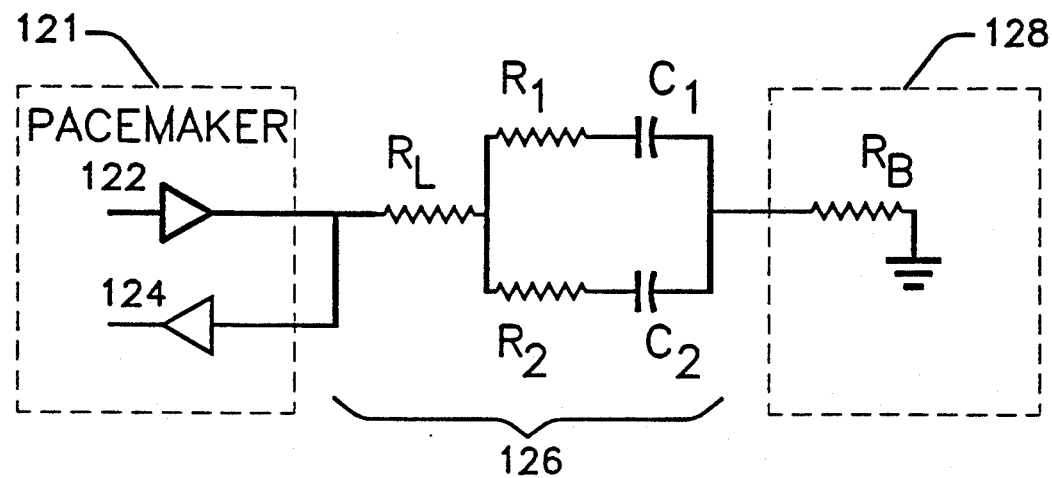
FIG. 14

LOW THRESHOLD CARDIAC PACING LEAD

FIELD OF THE INVENTION

The present invention relates in a broad aspect to the depolarization of excitable tissue. More particularly, the present invention is directed to methods of low energy pacing and effective sensing of the heart, and to an implantable lead that facilitates low energy pacing of the heart as well as effective sensing of electrical signals representative of the activity of the heart.

BACKGROUND OF THE INVENTION

Artificial pacemakers have been used for several decades to treat poor heart rhythms. One such arrhythmia is bradycardia. A person with this abnormality suffers from an unacceptably slow heart rate. This condition may be treated by implanting a pacemaker system to artificially increase the heart rate.

The pacemaker system consists of the pacemaker itself and a pacemaker lead. A pacemaker is a small electrical device implanted under the skin, usually below the collar bone. A pacemaker generates electrical impulses at a comfortable, life sustaining rate, 60 beats per minute for example. These impulses are transmitted from the pacemaker to the heart by the pacemaker lead. With the pacemaker output properly adjusted, each pulse causes the heart to beat.

A pacemaker may be constructed or programmed to operate in a variety of different modes. The simplest is the fixed rate mode. A pacemaker in this mode will generate pulses at regular intervals, irrespective of any conditions or responses. A fixed rate pacemaker set at 60 beats per minute will generate one pulse every second. Each beat is conducted along the lead and is transmitted to the heart muscle, also known as the myocardium. The myocardium immediately adjacent the tip of the lead becomes excited, that is it depolarizes. This initiates a series of physiological events that, in total, closely mimic the actions and results of an intrinsically generated heart contraction.

A more sophisticated pacemaker may be programmed to operate in response to the activity of the heart. The pacemaker will only emit a pulse to be conducted to the heart if the heart needs it. In other words, the pacemaker monitors the activity of the heart, and pulses only if the heart rate is too slow. In order to do this, the pacemaker circuitry must be informed of the activity of the heart. The lead performs this function. The lead, thus, performs two important functions in this instance; it allows the myocardial activity to be monitored and it allows pulses to be conducted from the pacemaker to the heart when needed. When a pacemaker is operating in this mode, it is operating in the inhibited mode. It will provide stimulation pulses to the heart at regular intervals unless it is inhibited by ongoing, intrinsic heart contractions.

The pacemaker lead is a flexible, insulated conductor with ends that are particularly suited to the functions they perform. One end must be electrically and mechanically connected to the pacemaker. Accordingly, it has any of a number of configurations that are standard in the pacemaker industry.

At the other end of the lead, the distal end, the lead must contact the heart electrically and mechanically. The manner in which the lead contacts the myocardium may have a profound effect on the efficiency with which the pacemaker pulse is conducted to the heart. A good interface (connection) will allow the heart to be paced with low energy and with little variation over time. This conservation of energy permits longer pacemaker battery life; thereby forestalling a subsequent operation to replace the pacemaker. A bad interface will require larger energy pulses to pace the heart and may, by virtue of the bad contact, cause physical trauma to the myocardium in the region adjacent the tip of the lead.

Past efforts at providing a good interface to the myocardium have resulted in continual improvements. An early standard among pacemaker leads had a smooth, hemispherical, metal electrode at the tip of the lead. This electrode served the dual purpose of pacing and sensing of the heart. At the time of implant the lead was positioned to a location that exhibited good pacing performance (as indicated by low energy depolarization threshold) and good sensing (as confirmed by relatively high voltage sensed signals). Over time, as the heart responded to this foreign body against it, a tissue reaction would ensue. This reaction effectively caused the formation of an unexcitable capsule immediately surrounding the electrode. The pacing threshold (the minimum pacing energy needed to result in a heart contraction) generally rose and then settled to an intermediate plateau; just as the immune system response flared in a large initial response to the foreign body and then subsided to a more stable intermediate level.

Largely through empirical observation, several factors were noted to affect the pacing threshold. Large mechanical stress on the heart resulted in the destruction of tissue adjacent the electrode. This destruction of tissue, known as necrosis, effectively moved the nearest excitable myocardial tissue further away from the electrode. In order to achieve a supra-threshold (successfully depolarizing) pulse, more energy needed to be delivered, since the pulse intensity diminishes roughly with the square of the thickness of the necrotic capsule.

It was noted that for a given lead stiffness, the size of the electrode had an effect on the size of the necrotic capsule that formed around the electrode. A very small electrode was perceived by the heart to be as an arrow; that is, very high stress was induced. A very large electrode was wasteful of the energy it delivered; that is, despite low stress on the heart, it used a great deal of energy because the current needed to be spread over such a large area. An optimum electrode surface area was found to be approximately 9 mm$^2$.

It was also noted that the surface finish of the electrode had an effect on the threshold. Evidently, a small amount of surface roughness or porosity allowed the body to quickly and efficiently stabilize the electrode with respect to the heart with only a thin necrotic capsule. The in-growth of tissue to the electrode surface apparently minimized shear stress on the heart, and so permitted lower pacing thresholds.

Electrode material was also noted to have effects on the pacing threshold and also on sensing effectiveness. The early pacemaker electrodes displayed a large degree of residual voltage polarization following pacing pulses. Research revealed that some materials displayed better pacing and sensing characteristics.

Other factors have been discovered to improve the effectiveness of pacing and sensing as well as simplifying the placement of leads. Some electrode shapes were shown to create lower thresholds, by creating higher local current intensities for example. Other leads reduced the immune system response to the electrode by eluting an immuno-suppressant at the myocardial interface. Still other leads made lead positioning simpler and more stable by incorporating an anchor by the electrode, typically a tiny corkscrew. Such leads are called active fixation leads.

Nonetheless, there remains a great need to create pacing leads with lower pacing thresholds and good sensing capability. There are several reasons why these improvements are needed. The reasons are basically of two sorts; (1) to improve the reliability and efficiency of state of the art pacing systems and (2) to introduce technology which will allow the state of the art in pacing technology to be extended.

Virtually every pacing system would benefit if pacing thresholds could be reduced without compromising safety or cost. Lowering the pacing threshold would imply that the pacer output could be reduced. This in turn implies longer pacer life and thus more reliability and safety for the patient.

In most patients, the pacing lead or leads are placed and the pacer is programmed so that pacing and sensing are both well performed. In some patients however there are difficulties. Some patients display abnormally high thresholds or loss of capture. For these patients, there is an absolute need for low threshold leads. In other patients sensing is difficult. This is especially true in particular instances. For example, sensing in the atrium (one of the upper chambers of the heart) is almost always more difficult than sensing in the ventricle (one of the larger, more powerful lower chambers). Sensing unipolarly is almost always more difficult than sensing bipolarly (only one electrode in the respective chamber of the heart for unipolar versus two electrodes in the chamber for bipolar). One particularly challenging sensing application is found in single pass leads. Usually, if sensing and/or pacing of both atrium and ventricle is to be done (dual chamber pacing), one lead is placed in the right atrium and a separate lead is placed in the right ventricle. When a single pass lead is employed, only one lead is placed, and it is intended to service both chambers. In this instance, atrial sensing is particularly tenuous.

There is also a need to extend the state of the art in pacing leads. Presently, a single pacing electrode requires so much energy that it is simply impractical to consider placing more than one electrode in one heart chamber. If a pacing lead were available that consumed very little energy it would be practical to place more than one electrode in one chamber. This could result in lead designs that offer unprecedented benefits to the patient. For example, the risk of losing capture due to electrode migration, localized myocardial deterioration (as may be associated with an infarct) or necrosis would be enormously reduced. The availability of multiple pacing electrodes for a single chamber may prove quite effective in the application of anti-tachycardia pacing (pacing the heart in an attempt to interrupt dangerously fast heart rates). The use of multiple electrodes in a single chamber may even permit more physiologic pacing. In other words, it may allow a deployment of electrodes that, when correctly activated, promotes the effectiveness of the heart pumping by increasing the ejection fraction.

SUMMARY OF THE INVENTION

Accordingly, it is a particular object of the present invention to provide a construction for a cardiac pacing lead which will provide a lower pacing threshold than is achieved with conventional pacing leads.

It is a further object of the present invention to provide this improved pacing function with no degradation of the sensing function of the lead.

It is an additional object of the present invention to achieve these goals without the need for specialized pacers or connectors.

It is yet an additional object of the present invention to achieve low pacing thresholds and high sensitivity in active fixation leads.

It is a further additional object of the present invention to provide multiple pacing electrodes capability to a lead, in addition to the sensing capability; the purpose of the multiplicity of pacing electrodes being the provision of additional pacing capability within a given chamber of the heart.

These and other objects are achieved by the methods and constructions of pacer leads as described in the following preferred embodiments. The objects are achieved by incorporating several changes in lead construction. The pacing function and sensing function of the lead are largely separated to the benefit of both pacing threshold and sensing effectiveness.

This separation permits the reduction of the size of the necrotic capsule that forms around the pacing electrode. The separation also permits the use of smaller pacing electrodes which stimulate smaller regions, and therefore require less energy. This separation also permits the use of materials to concentrate the pacing energy where it is needed.

This separation also works to the benefit of the sensing function because the sensing electrode may be placed exactly where it will be most effective, independent of the optimal pacing electrode position. Similarly the size, shape, material and surface characteristics of the sensing electrode may be optimized irrespective of the pacing electrode.

The pacing leads produced in accordance with the methods and constructions of the present invention will have the capability of achieving lower than conventional pacing thresholds with no sacrifice in the quality of the sensed signal. This will permit reduction in energy consumption in pacing systems with absolutely no need for special hardware or software. It will also permit the practical use of multiple electrode pacing leads.

BRIEF DESCRIPTION OF THE DRAWINGS

The above and other aspects, features and advantages of the present invention will be more apparent from the following more particular description thereof, presented in conjunction with the following drawings wherein:

FIGS. 8A-8D show views of different embodiments of lead tips made in accordance with the present invention, in which the pacing electrodes of the tip are embedded in polymeric paraboloids;

FIG. 14 shows a simplified electrical schematic equivalent diagram of a lead tip made in accordance with a different embodiment of the present invention;

FIGS. 15A and 15B show diagrammatic views, partially in cross section, of embodiments of a lead tip of the present invention wherein a pacing electrode is shown on the longitudinal axis of the lead and a sensing electrode surrounds the pacing electrode on the lead tip, and further wherein the electrodes are coupled to the conductor of the lead body through resistive/capacitive interfaces, as shown in FIG. 14;

Corresponding reference characters indicate corresponding components throughout the several views of the drawings.

DETAILED DESCRIPTION OF EXEMPLARY EMBODIMENTS

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
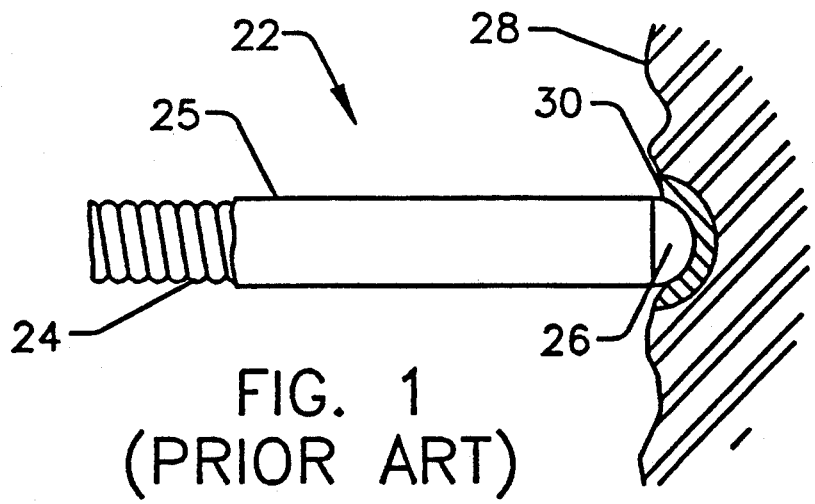
FIG. 1 diagrammatically shows a conventional lead and tip electrode positioned against heart tissue, with the heart tissue being diagrammatically shown in a cutaway view to demonstrate the chronic, fibrotic response to the presence of the electrode.
Figure 2:
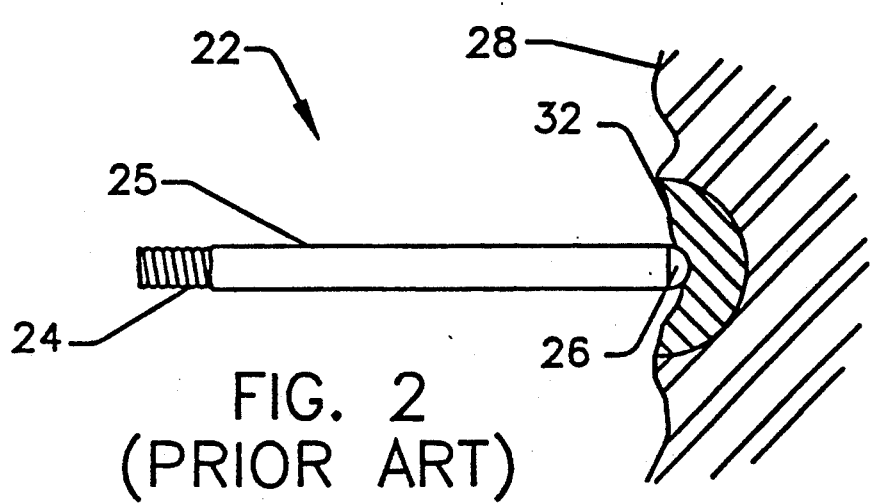
FIG. 2 diagrammatically illustrates a small diameter lead and tip electrode positioned against heart tissue, with the heart tissue again being shown in a cutaway view to demonstrate the chronic, fibrotic response to the presence of the electrode.

To better appreciate the problems associated with pacing leads of the prior art, reference is first made to FIGS. 1 and 2 where there is shown, in diagrammatic form, two types of pacing leads of the prior art. Each lead includes a lead body 22. The lead body 22 is made up of a helically coiled metal conductor 24, surrounded by an insulating sheath 25, that transmits electrical impulses to and from a roughly hemispherical tip electrode 26 or cylindrical proximal electrode (not shown). The excitability of cardiac tissue 28 adjacent the electrode 26 varies with time, partly due to the pressure necrosis caused by the electrode, as previously discussed. With currently available leads, having electrode surface areas of about 7-12 mm², a necrotic capsule 30 is formed having a thickness on the order of about 1 mm, as depicted in FIG. 1. Such surface area has been shown empirically to safely minimize the necrotic capsular response (given the stiffness of available leads). See Victor Parsonnet M.D., et al.; *Optimal Resources for Implantable Cardiac Pacemakers;* Circulation 68; No. 1, (1983).

It is known in the art to use a smaller electrode 26' to yield lower acute thresholds, as depicted in FIG. 2. Due to increased pressure caused by the smaller electrode, however, a thicker necrotic capsule 32 is formed and the effective pacing surface area is increased accordingly. Hence, the initial benefit of having a smaller electrode is quickly offset by the formation of the thicker necrotic capsule. Sensing is also more difficult through the smaller electrode of FIG. 2.

Figure 3:
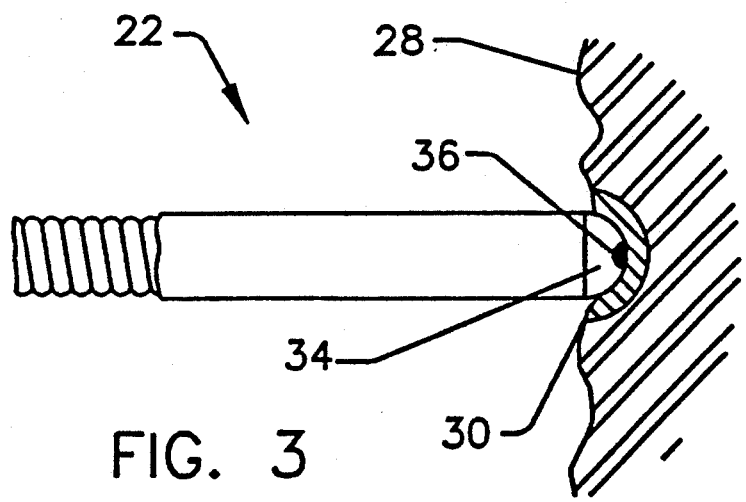
FIG. 3 diagrammatically illustrates a lead and tip electrode made in accordance with the present invention that is also positioned against heart tissue illustrated in a cutaway view as in FIGS. 1 and 2.

In accordance with the present invention, the stress on the heart is reduced by distributing the compressive force between the pacing lead and the heart over a larger surface area. Further, the pacing energy is minimized by using only a small portion of the surface area as the conductive pacing electrode. Hence, as shown in FIG. 3, a pacing lead tip made in accordance with the present invention includes, e.g., a conventional lead body 22 having a hemispherical tip 34 that has approximately the same surface area as the tip 26 (FIG. 1), but only a small portion of the surface area of the tip 34 functions as a pacing electrode 36. Compared to the electrode pictured in FIG. 1, the structure shown in FIG. 3 has the same fibrotic response. That is, the necrotic capsule 30 that forms as a result of the lead tip pressure is about the same as for the lead shown in FIG. 1. Advantageously, however, a smaller energy usage is needed for the lead tip shown in FIG. 3 since less current flow is needed to exceed threshold. That is, in both cases threshold is exceeded, but in the case of FIG. 1 much more tissue is depolarized and therefore, much more energy is used.

Figure 4:
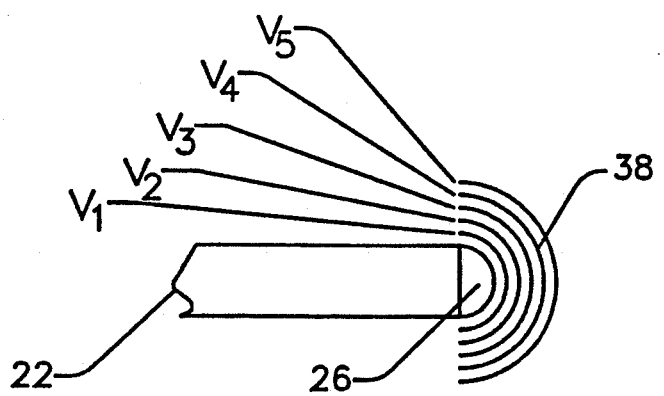
FIG. 4 represents an isopotential diagram showing the pattern of electric potential in the neighborhood of a tip electrode of a conventional pacing lead.
Figure 5:
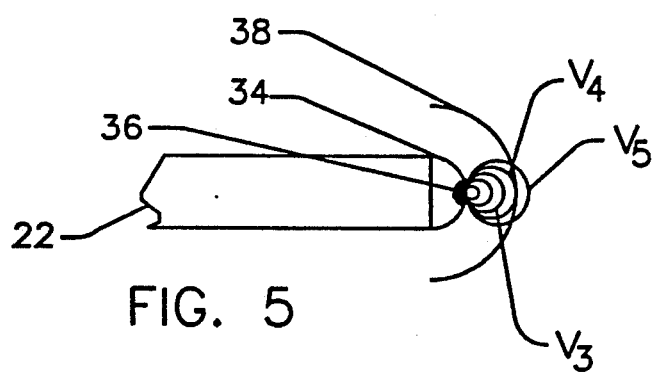
FIG. 5 represents an isopotential diagram showing the pattern of electric potential in the neighborhood of the tip electrode of a lead made in accordance with the present invention.
Figure 6:
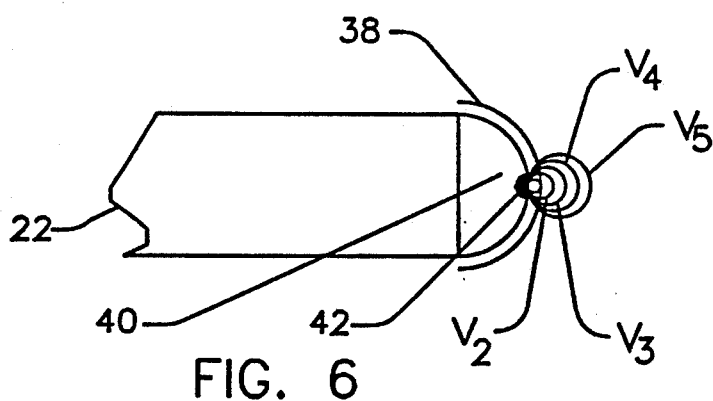
FIG. 6 represents another isopotential diagram showing the pattern of electric potential in the neighborhood of the tip electrode of another exemplary lead made in accordance with the present invention.
Figure 9:
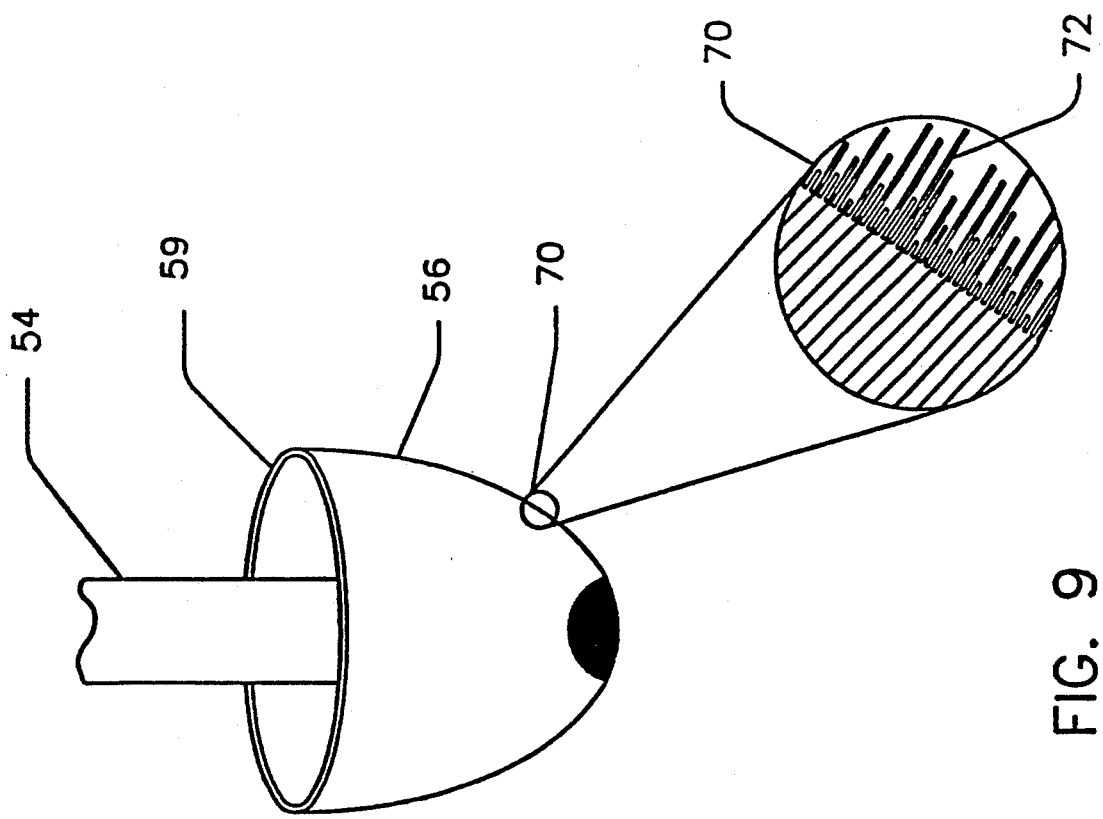
FIG. 9 shows a further view of a lead tip of the present invention in which the surface of the polymeric paraboloid has detailed features.

The advantage of using a small pacing electrode is further illustrated in FIGS. 4–6. FIGS. 4–6 show isopotential diagrams for several different types of electrode structures. Each of the lines $V_1$-$V_5$ surrounding the electrode tip structures shown in these figures represent a line of equal potential relative to the tip electrode. The bold isopotential line 38 represents the boundary of the necrotic tissue, and in order to excite (depolarize) the cardiac tissue, a voltage equal to or greater than the threshold voltage must be applied at this boundary. FIG. 4 illustrates the isopotentials for the prior art lead of FIG. 1. FIG. 5 represents the isopotentials for the lead tip configuration of the present invention, as shown in FIG. 3. Notice that in both FIGS. 4 and 5 a potential of $V_4$ may thus excite tissue. However, while the same voltage is required in both cases, much less current flows from the small electrode 36 of the lead tip shown in FIG. 5. In actuality, a slightly lower voltage may be required in FIG. 4 than FIG. 5 due to: (1) a less rapid decay of voltage with increasing distance from the electrode, and (2) the increased likelihood of exciting tissue closer to the electrode due to the variability in necrotic capsule thickness. However, while the prior art configuration of FIG. 4 may require slightly less voltage, it also requires massively more current. Thus, the lead tip configuration shown in FIGS. 3 and 5 is able to stimulate with much less energy.

An extension of the lead tip configuration shown in FIGS. 3 and 5 is shown in FIG. 6. The lead configuration shown in FIG. 6 includes a still larger surface area for the hemispherical tip 40 of the lead 22. A small electrode 42 forms part of the tip 40. Because of the larger surface area, the boundary 38 of the necrotic capsule is much closer to the surface of the tip 40. Hence, the pacing energy required to depolarize the cardiac tissue is reduced even further, e.g., to a level of around $V_1$.

It is thus an important feature of the present invention to reduce the necrotic capsular thickness that develops at the interface between an electrode and cardiac tissue. Such reduced thickness may advantageously be achieved by utilizing one or more of the constructions described below.

A first lead construction is as shown in FIG. 6. As seen in FIG. 6, and assuming that roughly the same scale is used in FIG. 6 as is used for the conventional pacing lead of FIG. 1, the diameter of the hemispherical tip 40 has been roughly doubled relative to the diameter of the hemispherical tip 26 of FIG. 1. This results in a surface area 4 times larger than the lead tip 40. Advantageously, by making the lead of FIG. 6 with such a large tip surface area, but with a only small pacing electrode 42, the stress on the heart is less due to the increased bearing surface. Thus, while the lead forces remain unchanged, such forces are spread over a larger surface area, thereby reducing the stress. Since the average compressive stress on the heart is equal to the total compressive force averaged over the contact area, the average compressive stress (pressure on the heart) is reduced. This results in a significantly reduced thickness of the necrotic capsule.

Figure 7:
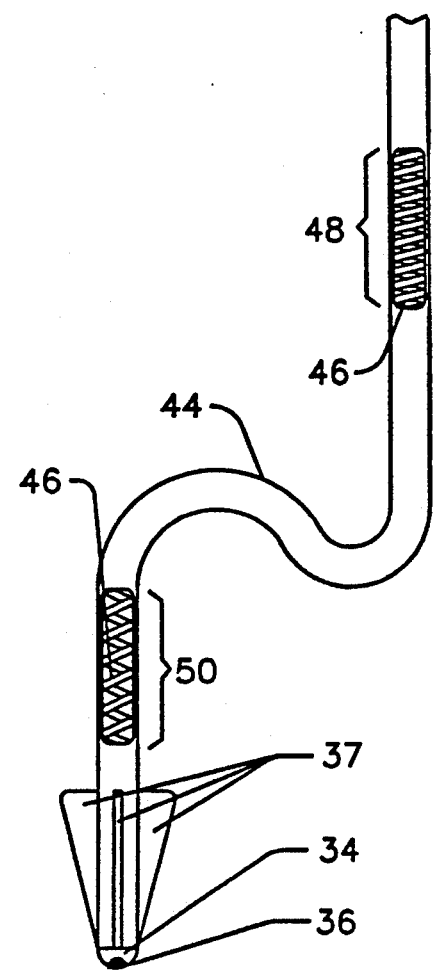
FIG. 7 shows one embodiment of a lead of the present invention shown in partial cutaway to reveal the variation in conductor wire winding pitch along the length of the lead.

A second lead construction that may be used to reduce the stress of the myocardium, and hence reduce the necrotic capsule thickness, is depicted in FIG. 7. In FIG. 7, a pacing lead 44 is shown having a tip 34 wherein a small electrode 36 is placed, as described above in connection with FIGS. 3 and 5. Fins 37 (or tines) may be positioned near the tip 34 in order to help hold the lead tip in position once placed within the heart, in conventional manner. Unlike the leads shown in FIGS. 3 and 5, however, the lead 44 shown in FIG. 7 utilizes a coiled conductor 46 therein that employs a different winding pitch at different locations along the length of the lead. Throughout most of the length of the lead 44, the pitch of the wound conductor 46 is closely wound, as shown generally in the cutaway region 48. However, near the distal tip 34 of the lead, as shown in the cutaway region 50, the conductor is wound with much greater spacing. This results in a different (lighter) force with which the tip 34 is held against the cardiac tissue.

With regard to FIG. 7, it is noted that conventional leads, once anchored to the heart, behave something like a dynamic spring-mass system. The reactive force on the heart, for a given heart motion, can be predicted. As depicted in FIG. 7, for example, the force on the heart is reduced to a lower level by constructing the lead 44 so that it essentially divides the lead into a dual mass-dual spring system. The damped natural frequency of such a system is tuned so that the transmissibility at physiologic frequencies is close to zero and the force on the heart is thus reduced.

As seen in FIG. 7, the stiff and flexible portions of the lead 44 are created simply by changing the pitch of the winding at the appropriate locations. In a similar manner the lead mass sections are divided by creating an intermediate soft leaf spring. The leaf spring is simply a serpentine section of the winding. Since the coiled conductor 46 deflects much more laterally (as a leaf spring) than axially, it is thus softer in that section. The variation in lead body stiffness may also be achieved by varying the filarity (number of individual conductors comprising the helix).

The lead configurations described herein, such as that shown in FIG. 7, advantageously reduce the force at the tip-electrode/cardiac-tissue interface. However, the physician who places the lead during the implant operation, is not necessarily aware that such tip-electrode/cardiac-tissue forces are reduced. This is a definite advantage because such leads are more readily acceptable clinically because the implanting physician does not need to change his or her perceptions of lead placement. Many physicians, as they perform the lead implant operation, like to feel the lead pressing firmly against the heart. It is precisely this force that is one major cause of the necrotic capsule that forms around the electrode. Hence, it is frequently this "implant force" that prevents the lead from functioning to the limits of its capabilities. By utilizing lead constructions as taught herein, the actual force at the tip-electrode/tissue interface can be reduced even though the implant force may "feel" the same to the physician.

Other lead configurations of the present invention also reduce the stress or force at the electrode/tissue interface. For example, as described more fully below in connection with FIGS. 11 and 12, the electrode may be moved to a site remote from the zone where the lead tip contacts the cardiac tissue (the "contact zone"), thereby avoiding the thickest section of necrosis. As with a conventional pacing lead, there is a large, stabilizing force between the lead tip and the heart. Unlike conventional leads, however, the pacing electrode is situated at a site removed from the site of mechanical trauma. For example, the electrode may be situated in a low spring constant leaf spring that projects radially from the lead body. Such a leaf spring advantageously provides only enough force to hold the electrode against the heart without the need to provide sufficient force to stabilize the entire lead tip.

Further, it should be noted that motion of the lead tip relative to the heart, even motion at a microscopic level, may create shear stress, and thereby increase necrosis and decrease pacing reliability. Accordingly, it is known in the art to incorporate means of microstabilization. Unfortunately, however, due to the use of conventional lead tips, such stabilization has been limited to stabilizing a hard lead tip against the soft myocardium a compliance mismatch. That is, conventional electrode designs utilize materials at the myocardial interface which are many times stiffer than the heart. For that reason, and also due to the geometry of the lead tip, the load on the heart is high and includes sharp changes in stress. These conditions promote immune system response that increase the fibrotic response and thus the distance from the electrode to excitable tissue.

In order to address this problem, the present invention provides lead tip designs that incorporate the electrode tip in soft materials that best match the heart tissue. Examples of such lead tip designs are shown in FIGS. 8A-8D and 9. In general, the designs shown in FIGS. 8A-8D and 9 use flexible materials and atraumatic geometries that permit smooth and broad distribution of stress on the heart. The use of polymers at the lead tip lowers stress on the heart. Some metal is usefully incorporated into the tip design so that the composite tip splits the load between the metal and polymer. Certain macro and micro geometries are also used to promote stabilization. The use of a controlled release agent from the tip may also be used in some configurations as an aid in reducing fibrotic response as the lead tip anchors to the heart.

Figure 8D:
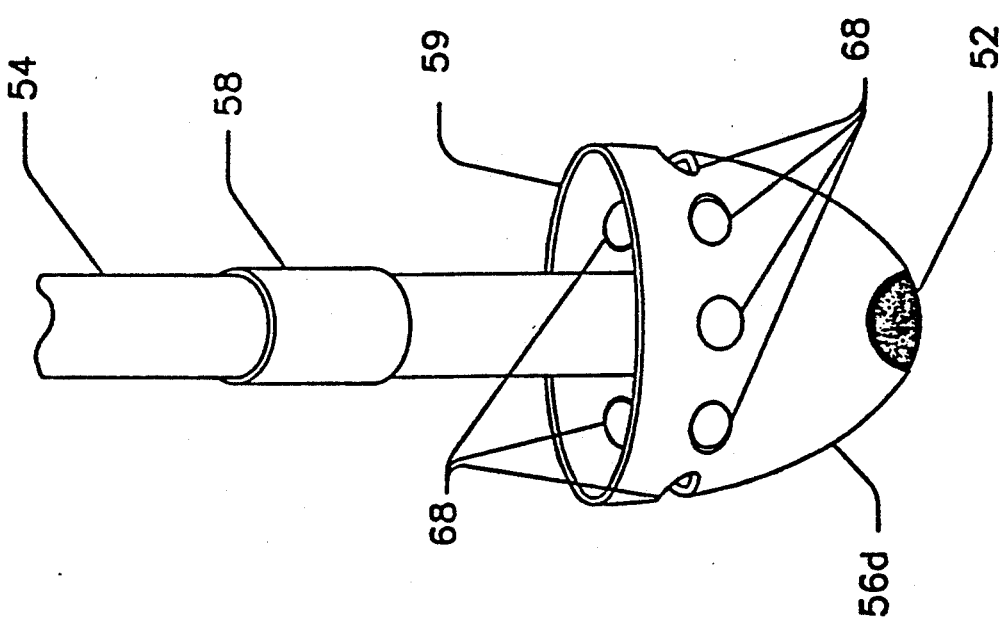

Since pacing leads are often placed in areas of small radii of curvature (e.g., ventricular apex and atrial appendage) it is possible to assure contact near the edges of the lead tip and yet still more uniformly distribute the load. As an example, by using a lead that has an electrode with tip radius that is slightly larger than the local radius of curvature of the heart, contact is assured at the edges of the tip. Depending on the tip shape and stiffness, the best location for a pacing electrode may be at the tip of the electrode or near the edge. With a lead tip of such construction, the maximum stress on the heart and the average stress on the heart are both greatly reduced. Pressure is significantly reduced at the electrode, or effectively preselected to be in an optimum pressure range, by putting the electrode at a site removed from the lead tip. The pressure is further refined by designing the lead tip so that it provides enough pressure to assure good contact while maintaining the pressure at a sufficiently low level to minimize necrotic response. Turning to FIGS. 8A-8D and 9, a lead tip construction is shown wherein the pacing electrode(s), comprising a relatively small portion of the surface area of the lead tip, are embedded in polymeric paraboloids. In FIG. 8A, an electrode 52 is located at the tip of a hollow polymeric paraboloid 56a. The paraboloid 56a is formed at the distal end of a lead body 54. A ring electrode 58, is located on the body of the lead 54 so as to be spaced apart from the tip electrode 52. Such ring electrode 58 may be used as a conventional ring electrode, as is commonly used in bipolar pacing, or as a sensing electrode, in the manner described below. The paraboloid 56a is made from silicone rubber, polyurethane, or other soft polymer substance that is compatible with body fluids and tissue, and is adapted to readily conform to the shape of the heart with minimal force. The paraboloid material becomes progressively thinner as it approaches the edge 59 of the paraboloid. Thus the pressure becomes less as the edges are approached. Advantageously, the paraboloid shape allows easy entrapment within the trabeculae of the heart for acute stabilization.

To further promote stable positioning and tissue in-growth, the tip geometry may be varied, as shown in FIGS. 8B-8D. In FIG. 8B, for example, a paraboloid 56b is employed having a plurality of slits 60 placed therein that run from the paraboloid edge 59 towards the electrode 52, thereby forming petals 62.

In FIG. 8C, a paraboloid 56c is employed having a pair of wider slits or slots 64 that divide the paraboloid 56c into wings 66. An electrode 53 is positioned within one of the wings 66, away from the tip of the paraboloid. A similar electrode (not visible in FIG. 8C) may be positioned in the other wing(s) 66 of the lead tip.

In FIG. 8D, a paraboloid 56d is employed having a plurality of holes 68 and/or dents placed therein.

The surface of any of the above paraboloids may be microporous for good chronic micro- stabilization (via tissue in-growth) for low thresholds. As an alternative to porosity, the surface may have protuberances 72 to minimize fibrotic response. Such protuberances 72 are diagrammatically illustrated in the inset 70 of FIG. 9, which inset 70 shows a greatly magnified side view of the surface of a paraboloid 56. Such protuberances 72 advantageously allow tissue in-growth, and in addition they further reduce the load on the heart by acting as a stress relief (or cushion). The manner of making such protuberances 72 is known in other arts, such as implantable release polymers.

Figure 10B:
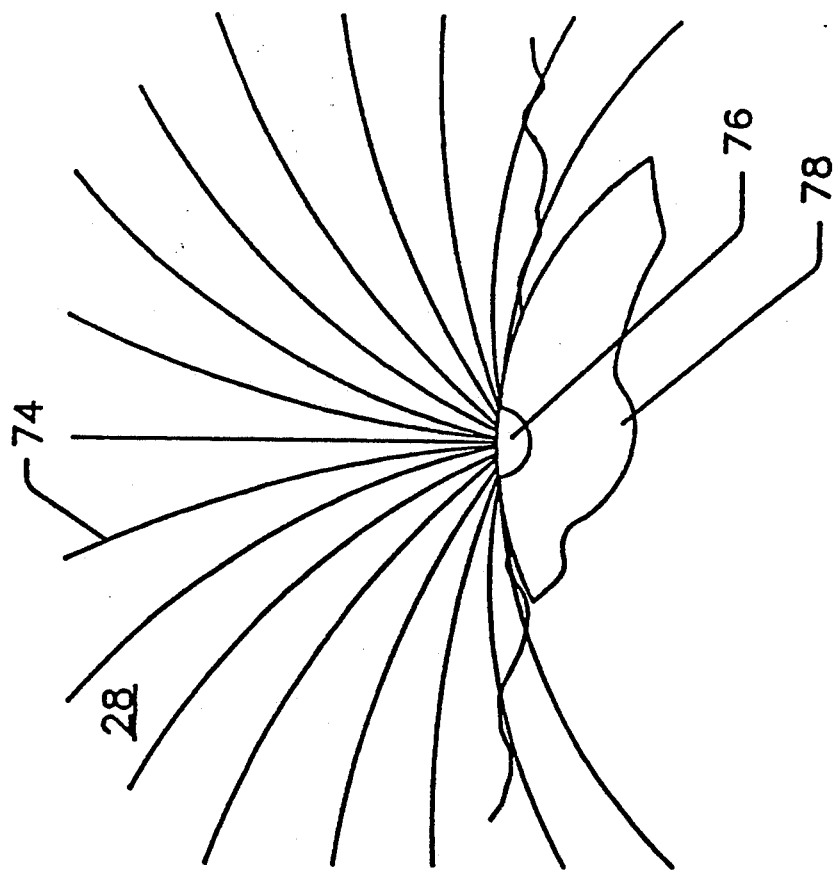
FIGS. 10A and 10B show lines of current flux emerging from a pacing electrode of a conventional lead and a pacing electrode of a lead of the present invention, respectively.
Figure 10A:
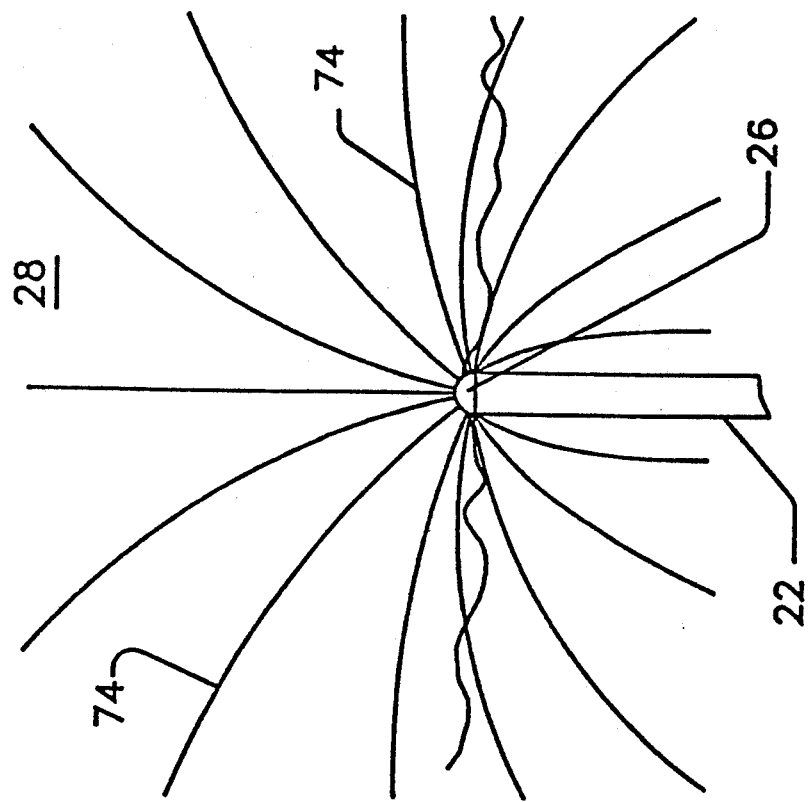

As is known to those of skill in the art, the electric field intensity drops off rapidly with increasing distance from the pacing electrode. The present invention advantageously provides a configuration wherein the rate of decay of the electric field is reduced, thereby allowing stimulation to be achieved with less energy. Among the factors influencing the electric field intensity are the electrode geometry and the dielectric constants of the interposed materials. In the immediate vicinity of a unipolar tip electrode the E-Field resembles that of a point charge in a vacuum. This is illustrated in FIG. 10A, where current flux lines 74 spread out from the unipolar tip 26 of the lead 22, tending to bend toward the lower resistance blood rather than pass directly through the myocardial tissue 28. A much more effective approach for pacing is to force the E-field to be more concentrated in front of the electrode, and by so doing push more of the energy into the myocardial tissue 28), as depicted in FIG. 10B. In FIG. 10B, a small electrode 76 is located on the tip of the pacing lead 78. The lead 78 is made from an appropriate material, selected to provide an appropriate dielectric constant having a higher impedance than the myocardial tissue. The polymer from which the sheath 25 of a pacing lead is made satisfies this requirement. The lines of flux 74 associated with the E-field are thus forced out away from the electrode towards the myocardial tissue 28, with the lines of flux associated with such E-field preferentially remaining in the relatively conductive myocardium and avoiding the high impedance, high dielectric polymer, thereby producing an intensified field in the excitable tissue.

Figure 11:
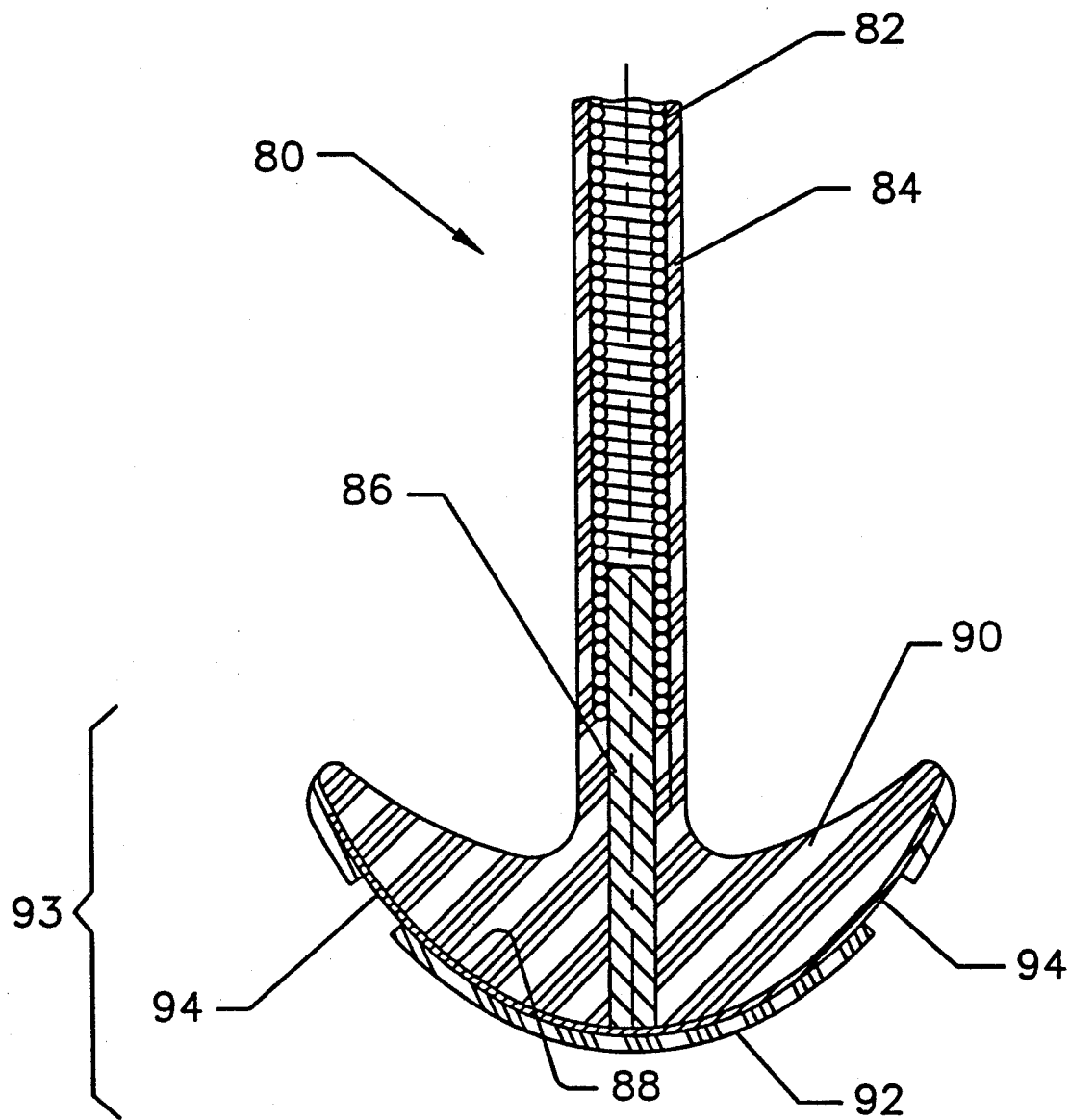
FIG. 11 shows a diagrammatic view, shown partially in cross section, of one embodiment of a lead tip made in accordance with the present invention wherein a plurality of pacing electrodes are placed off the longitudinal axis of the lead.

Referring to FIG. 11, a particular lead construction is illustrated that incorporates the features of the invention described above. The lead construction includes a lead body 80 having a helically wound conductor 82 covered with a non-conductive insulative sheath 84. An electrode core 86 is crimped to the conductor 82 at one end, and is welded, brazed or otherwise bonded at its other end to a flexible, foil electrode 88. The electrode 88 is backed with a paraboloid shaped backing 90, made from the same, or equivalent, material as the sheath 84. The front of the electrode 88 is likewise covered with a thin, flexible, non-conductive layer 92. The electrode 88, backing 90, and covering layer 92 comprise the head 93 of the pacing lead. At selected locations on the layer 92, an opening 94 is made to expose the electrode 88. The exposed portions of the electrode 88 comprise the small electrode surface that is used to contact body tissue in accordance with the present invention. The openings 94 are strategically located on the surface of the head 93 so as to expose only those areas where the electrode surface is desired. For example, the openings 94 may comprise a plurality of small openings, e.g., 4–8 openings selectively positioned around the front surface of the head 93. Alternatively, a single annular opening 94 may be made to provide an annular electrode surface.

The sheath 84 and backing 90, may be made from any suitable polymer, such as silicone or polyurethane. The cover 92 may also be made from these polymers, or from high strength polymers which may be made in very thin films (about 0.001 inch thick) such as polyethyler or mylar. The electrode 88 is preferably made from a thin conductive foil, 0.0005–0.0010 inches thick, such as a platinum or elgiloy foil. The electrode core 86 may be made from any of a variety of conductors, such as platinum or stainless steel, titanium, etc., having an outside diameter suitable to fit within conventional lead conductor coils of from 0.02 to 0.08 inches. The same fabrication techniques used to make conventional pacing leads may also be used to make the lead configuration shown in FIG. 11, or equivalents thereof.

Advantageously, the lead constructions described above do in fact provide pacing leads that stimulate the heart with lower acute and chronic thresholds. However, the leads as described thus far do not specifically address the sensing function. Disadvantageously, the small surface area, low resistance pacing electrodes as described thus far are well suited for pacing, but not necessarily for sensing. The ideal sensing electrode, to the contrary, should be much larger than the ideal pacing electrode. This is because the pacing function is best served by a low impedance small surface area electrode, while the sensing function is best served by a high impedance large surface area system.

Advantageously, the present invention further includes sensing electrodes that allow the sensing and pacing activities to be separated so that each can best provide a surface area and accompanying impedance that best meets its intended function. An example of a lead tip that includes such sensing and pacing features is depicted in FIG. 12.

Figure 12:
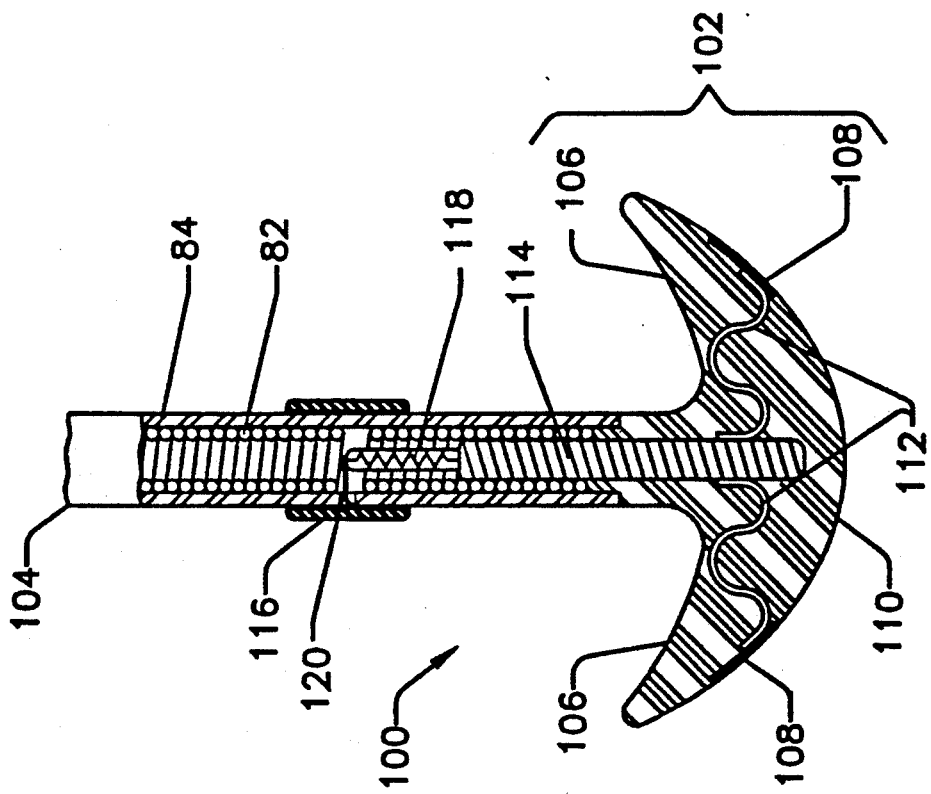
FIG. 12 shows a diagrammatic view, shown partially in cross section, of another embodiment of a lead tip of the present invention, in which a plurality of pacing electrodes are placed off the longitudinal axis of the lead; and a sensing electrode, electrically connected to the conductor coil of the lead through a discrete resistor, is positioned proximally on the lead body.

As seen in FIG. 12, a lead tip 100 is shown that includes an umbrella-shaped head 102 attached to a lead body 104. The lead body 102 is of conventional design, including a wound conductor 82 covered with a non-conductive, insulative sheath 84. The head 102 is made of a material, the same or similar as the sheath 84, that is non-conductive, insulative, pliant, and bio-compatible, such as silicone or polyurethane. As seen in FIG. 12, the head 102 extends out from the lead body 104, much as an umbrella extends out from an umbrella shaft. The edges or tips 106 of the head 102 are pliant and can readily fold over and lie against the body 104 during implantation, thereby allowing the lead to be inserted through openings not much larger than the diameter of the lead body, when necessary. However, the head 102 is formed so that in the absence of a constraining space, the tips 106 of the head 102 extend out away from the body 104 as depicted in FIG. 12. Such tips 106 thus serve the function of tines or fins to help hold the head 102 in a desired location.

One or more small pacing electrodes 108 are selectively positioned in the front on the head 102 at the head tips 106. Such placement advantageously moves the electrodes 108 away from the apex 110 of the head 102, and thereby possibly away from the axis of the lead body 104 and the point of highest physical stress. The electrodes are made from any suitable conductor that is compatible with body fluids, such as platinum, elgiloy, carbon, titanium, etc., embedded in the non-conductive, flexible, material from which the head 102 is made. The exposed surface of the electrodes 108 may be porus and/or roughened to promote tissue ingrowth. A conductive strip of wire 112 electrically connects the electrodes 108 to a conductive shaft or rod 114 that is tightly held in physical and electrical contact with the lead conductor 82.

The lead tip shown in FIG. 12 further includes a ring electrode 116 positioned behind the lead head 102 so as to be positioned around the lead body 104. This ring electrode 116 functions as a sensing electrode. The sensing or ring electrode 116 is electrically connected to the lead conductor 82 by way of a resistor 118 and a wire 120. One end of the wire 120 is welded, bonded or otherwise electrically connected to the inside surface of the ring electrode 116. The other end of the wire 120 is connected to one end of the resistor 118. The other end of the resistor 118 is attached to the conductive rod 114. One of the purposes of the resistor 118 is to divert most of the pacing current through the pacing electrodes 108, rather than through the sensing electrode 116.

In making the head 102, the rod 114 is inserted inside of the wound conductor 82. Appropriate crimping or welding techniques may be used to establish a good electrical connection between the conductor 82 and the rod 14. The conductor 82, and rod 114 may then be mounted in an appropriate holding fixture, along with the electrodes 108, wires or ribbons 112, resistor 118, and wire 120. Such holding fixture also functions as a mold for forming the head 102. Then, the non-conductive material from which the head 102 is made is injected or otherwise placed within the holding fixture in a liquid state, allowed to cure, thereby forming the umbrella-shaped head 102.

For pacing, most energy leaves the electrode (by current division) through the low resistance pacing electrode 108. In sensing, the pacing electrode 108 will still conduct, though it may polarize, in which case the large surface area of the sensing electrode will continue to sense without polarizing nearly as much. When a pacing stimulus is delivered, the output impedance of the pacemaker circuits is low. During sensing the input impedance of the sense amplifiers within the pacemaker is very high (much higher than the resistance of the lead and the physiological return path through the conductive body fluids and tissue), and the sense current is thus very low.

Variations of the approach shown in FIG. 12 ——of having a low impedance pacing electrode and a high impedance sensing electrode——may also be used in accordance with the present invention. For example, the outer surface of the lead tip may be a surface that is deposited to have areas of moderate resistance with small selected sites of low resistance. The areas of moderate resistance would function as the sensing electrode, and the sites of low resistance would function as the pacing electrode.

For the embodiment of the lead tip shown in FIG. 12, or equivalents thereof, it is desired that the resistance pathway through the sensing electrode be much higher than the resistance pathway through the pacing electrode. That is:

$$R_L + R_P + R_{B1} << R_L + R_S + R_{B2} \quad (1)$$

where
$R_L$ = Lead Resistance
$R_P$ = Pacing Electrode Resistance
$R_{B1}$ = Body Resistance (Pacing)
$R_S$ = Sensing Electrode + Discrete Resistor 118
$R_{B2}$ = Body Resistance (Sensing)

$R_L$ is virtually identical whether sensing or pacing. $R_{B1}$ is greater than $R_{B2}$ primarily due to the difference in surface area at the body interface, therefore $R_S$ must be much larger than $R_{B1}-R_{B2}$. In most sensing electrodes of the prior art, where an attempt is made to use separate pacing and sensing electrodes, a high $R_S$ has been achieved by selecting the material property of the sensing electrode. As evident from Eq. (1) above, however, the value of $R_S$ is determined by the discrete resistor 118 as well as the sensing electrode. Use of the resistor 118 thus simplifies the choice of materials for the sensing electrode.

Figure 13:
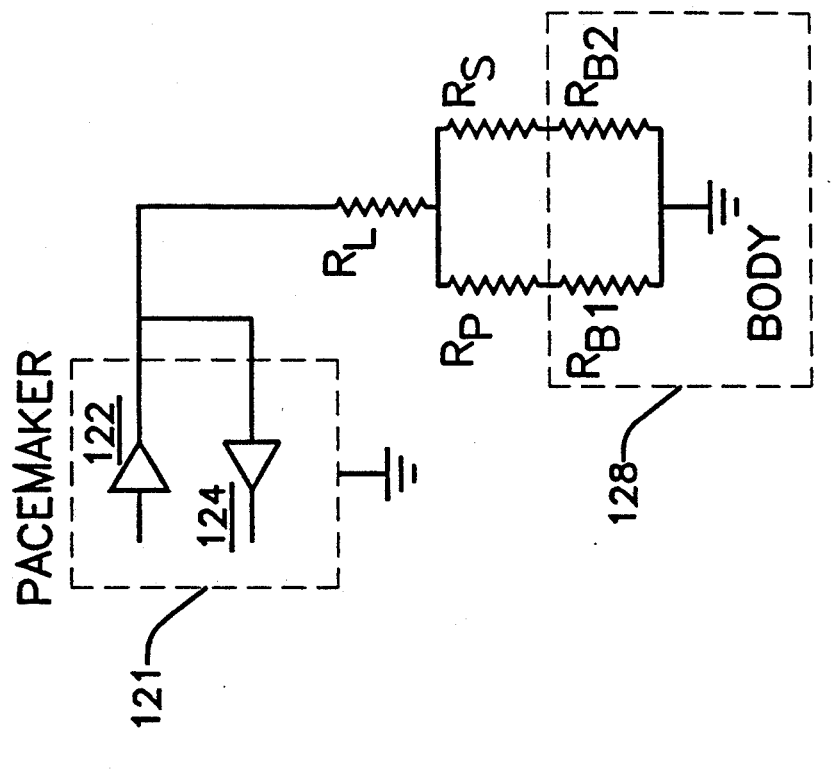
FIG. 13 shows a simplified electrical schematic equivalent diagram of the lead tip shown in FIG. 12.

An electrical equivalent diagram of the sensing and pacing circuits associated with a pacing/sensing lead made in accordance with the present invention is shown in FIG. 13. The resistance symbols shown in the FIG. 13 are the same as those used above in connection with Eq. (1). A pacemaker 121 includes a pace amplifier 122 than has a very low output resistance; as well as a sense amplifier 124 that has a very high input impedance. The lead resistance $R_L$ is shared between the pacing and sensing functions. The sensing resistance $R_S$ should be made much larger than the pacing resistance $R_P$. Typically, the total pacing resistance $(R_L+R_P+R_{B1})$ may be on the order to 100–1000 ohms. The input impedance to the sense amplifier 124 may be on the order of 20K ohms or more. Hence, a representative value for the sense resistor $R_S$ is on the order to 10K ohms, which is much greater than the pacing resistance and much less than the sensing amplifier input resistance.

Advantageously, placing the sensing electrode 116 away from the pacing electrode 108 further enhances the sensing function by reducing the formation of a charged surface layer on the sensing electrode.

The voltage that appears on the sensing electrode 116 is due in part to a voltage divider, as is evident from the equivalent circuit diagram shown in FIG. 13. The sensed voltage is also a function of the strength of the electric field created by the much higher voltage pacing electrode. By separating the pacing electrode 108 from the sensing electrode 116, the extraneous voltage on the sensing electrode 116 is reduced, thereby reducing after-potentials and polarization. In other words, the separated pacing and sensing electrodes provide enhanced sensing.

It is appreciated by those skilled in the art that although this may appear to be similar to a bipolar electrode, it is unipolar. A bipolar lead of course could be constructed using conventional technology for the remote anode. Pacing leads of the present invention could equally well be constructed bipolarly or unipolarly.

The lead construction shown in FIG. 12, and equivalents thereof, seeks to save energy and improve sensing by pacing from a small electrode while sensing from a large electrode. Obviously, such pacing and sensing could be accomplished using separate, insulated electrodes. However, separate, insulated electrodes would require separate conductors, if not separate connectors (or at least bipolar style connectors). It is much more advantageous and practical to achieve the paradox of discrepant pacing and sensing electrode sizes on a single lead using a single conductor, as described herein.

Other embodiments of the invention provide for separating the functions of pacing and sensing in a single lead by using other criteria, in addition to resistance. For example, the frequency content of the pacing signal is vastly disparate from the frequency content of the sensing signal. The bulk of the sensed signal is normally contained below 100 Hz. Most of the energy of a pacing pulse is (or easily could be) above 500 Hz. Hence, any approach that could separate a low frequency sensing signal from a higher frequency pacing signal, such as passive filtering, may be employed within a pacing lead made in accordance with the present invention. Doing so allows the use of low energy pacing and avoids the need for separating the pacing and sensing signals at the sense amplifier of the pacemaker. Further, there is a huge benefit to separating the signals at the electrode itself.

Hence, in accordance with another embodiment of the present invention, a pacing/sensing lead is provided having both pacing and sensing electrodes wherein the pacing electrode has negligible impedance (a function of electrical resistance, capacitance and inductance) at high frequencies and the sensing electrode has very high impedance at those frequencies. Since the lead resistance is nearly the same for pacing and sensing, the desired difference in impedance is achieved by incorporating different capacitances over the respective areas of the electrode, independent of or in addition to the varied electrode resistance as previously indicated, Such an approach, of incorporating different capacitances, is illustrated in the equivalent electrical schematic diagram of FIG. 14. In FIG. 14, the pacemaker 121 is connected to body tissue 128, represented by the body resistance $R_B$, through a pacing/sensing lead 126. The pacing/sensing lead 126 includes a lead resistance $R_L$; a pacing electrode resistance $R_1$ in series with a first capacitor $C_1$ (the "pacing RC network"); and a sensing electrode resistance $R_2$ in series with a second capacitor $C_2$ (the "sensing RC network"). The pacing RC network is in parallel with the sensing RC network, with both RC networks being in series with the lead resistance $R_L$, Both the pacing RC network and the sensing RC network function as passive low pass filters in coupling a signal from the pacemaker 121 to the body tissue 128, or from the body tissue 128 to the pacemaker 121. That is, the cutoff frequency of the sensing RC network is selected to pass only signals that are, e.g., 100 Hz or less. The stimulation pulses, which may have a frequency (spectral) content above 500 Hz, are thus not efficiently coupled to the body tissue 128 through such sensing RC network. (It is noted that if the pacer is pacing at, e.g., 60 pulses per minute, or one pulse/sec, there is a primary or fundamental frequency component at that low frequency. However, there is very little power at that frequency, so little of the pacing energy is wasted or lost.)

Exemplary embodiments of the above approach are shown in FIGS. 15A and 15B. FIGS. 15A and 15B show diagramatic views, partially in cross section, of embodiments of a lead tip of the present invention wherein a pacing electrode, coupled to the body tissue through a capacitive/resistive interface, is positioned on the longitudinal axis of the lead; and a sensing electrode, comprising a sensing electrode that is similarly coupled to the body tissue through a capacitive/resistive interface, surrounds the pacing electrode on the lead tip. In FIG. 15A, for example, a lead body 130 includes a wound conductor 132 inside of an insulating sheath 134 in conventional manner. The lead conductor 132 is connected to an electrode core 136, comprising a rod made of a suitable conductive material. The distal tip 137 of the electrode core 136 is covered with a non-conductive, dielectric material 1.38, such as epoxy, mylar or polyurethane, with the non-conductive material 138 being the material that physically contacts the body tissue 28 when the lead is implanted. Advantageously, the non-conductive material 138 functions as the dielectric of a capacitor $C_1$, with the distal tip 137 of the conductive core 136 functioning as one plate of the capacitor, and the conductive body tissue 28 functioning as the other plate of the capacitor. The combined resistance of the lead conductor 132 and the core material 136 determine the value of $R_1$, with the $R_1C_1$ values determining the cutoff frequency of the filter thus formed.

Similarly, the lead conductor 132 is connected to a conductive electrode ring 140 that surrounds the core 136. The tip of the electrode ring 140 is dome-shaped and is covered with an insulative, dielectric material 144. For the embodiment shown in FIG. 15A, the dome-shaped surface of the electrode ring 140 does not contact the body tissue 28 when the lead is implanted. Rather, the dielectric material 144 functions as the dielectric of a capacitor $C_2$, with the dome-shaped surface of the electrode ring 140 functioning as one plate of the capacitor $C_2$, and the body tissue 28 functioning as the other plate of the capacitor $C_2$. The combined resistance of the lead conductor 132 and the conductive electrode ring 140 determine the value of $R_2$, with the $R_2C_2$ values determining the cutoff frequency of the sensing filter thus formed.

As thus seen in FIG. 15A, an electrode tip is disclosed wherein $R_1C_1$ is selected to optimize pacing through a small surface area electrode aligned with the lead axis, and $R_2C_2$ is selected to optimize sensing through a larger surface area electrode that surrounds the pacing electrode. These resistance and capacitive values are likewise selected to minimize cross talk. A bleed resistor (which may comprise small holes through the dielectric to expose the underlying resistor) may be provided, as required, to avoid excess charge accumulating on the capacitors $C_1$ and $C_2$.

It is to be appreciated that $R_1$ may be different from $R_2$ but need not be so by necessity. It is also to be appreciated that one of the capacitors may be deleted to further improve low frequency response.

FIG. 15B depicts a variation of the embodiment of the capacitive lead electrode of FIG. 15A. The electrode shown in FIG. 15B is essentially the same as the electrode shown in FIG. 15A except that, for ease of construction, the dielectric layer 144 has been removed, thereby effectively eliminating the sense capacitor $C_2$(FIG. 14). The capacitor $C_2$ can be eliminated if its complex impedance is much lower than the resistance $R_2$. In addition, without the $C_2$ layer, any need for a bleed resistor is unnecessary.

Figure 16:
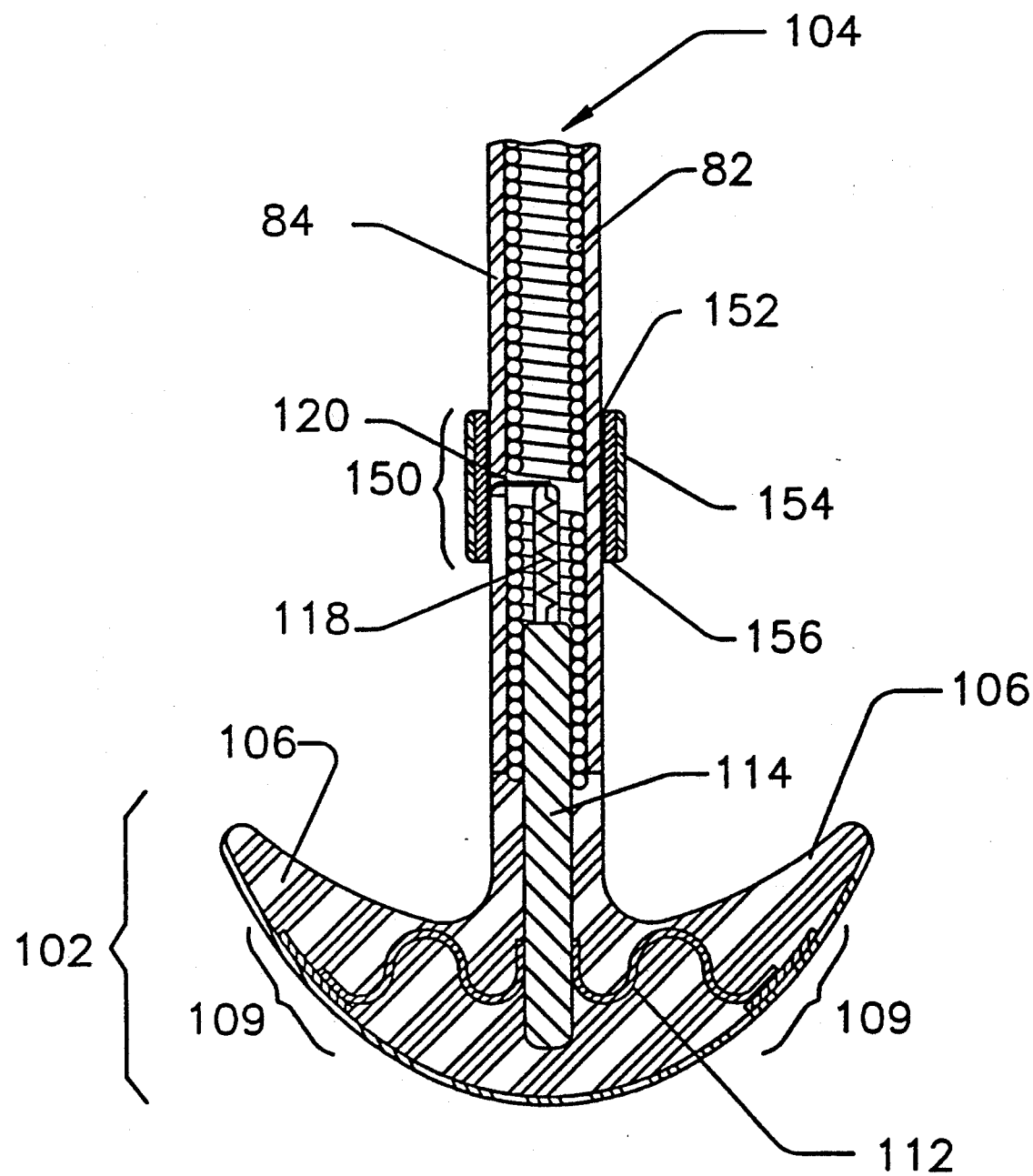
FIG. 16 shows a diagrammatic view, partially in cross section, of still another embodiment of a lead tip of the present invention having a plurality of pacing electrodes placed off the longitudinal axis of the lead and a sensing electrode placed proximally on the lead body, and further wherein the pacing and sensing electrodes are coupled to the conductor of the lead body through resistive/capacitive interfaces.

Referring next to FIG. 16, a variation of the capacitive coupling electrode configuration is illustrated. The lead configuration shown in FIG. 16 is similar to the lead configuration shown in FIG. 12, described above, and corresponding reference numerals are used to describe equivalent parts. The difference between the lead configuration shown in FIG. 16 from that shown in FIG. 12 relates to the sensing and pacing electrodes. In FIG. 16, the pacing electrodes 109 comprise two metal plates 144 and 146 separated by a suitable dielectric 148, thereby forming a capacitor $C_1$. Similarly, the sensing electrode 150 comprises two concentric metal rings or layers 152 and 154 separated by a dielectric layer 156, thereby forming a capacitor $C_2$. As with the other capacitive coupling embodiments (FIGS. 15A and 15B), a bleeder resistor may be used, as required, in order to prevent the build up of excess charge on the sensing electrode 150 or the pacing electrode 109.

Another way to construct an electrode with the same effectiveness is to use a single resistor for the electrode with two distinct capacitive layers. This allows the resistance to remain low so that the total impedance for both sensing and pacing can be very low at the respective frequencies. A capacitively coupled lead made in this manner could be combined with a low pressure pacing electrode as described above.

Figure 17A:
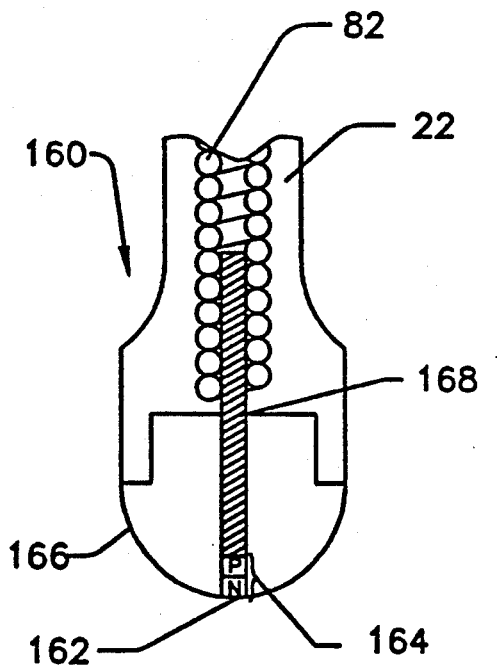
FIG. 17A shows a diagrammatic view, partially in cross section, of another lead tip of the present invention having a lead tip that includes a pacing electrode comprising a P-N diode and a sensing electrode surrounding the pacing electrode.

FIG. 17A shows a diagrammatic view, partially in cross section, of yet another embodiment of a lead tip made in accordance with the present invention that may be used to achieve separation of the sensing and pacing functions. The embodiment of FIG. 17A has a lead tip 160 that includes a pacing electrode 162 comprising a P-N diode 164, and a sensing electrode 166 surrounding the pacing electrode. The P-N diode 164 is in electrical contact with a conductive core piece 168. The conductive core piece 168, in turn, is connected directly to the wound conductor 82 of the lead 22. Also connected to the conductor 82 is one end of the sensing electrode 166. As seen in FIG. 17A, the sensing electrode 166 comprises an annular dome piece that surrounds the P-N diode 162 and conductive core piece 168. The dome piece 166 is made from a conductive material selected to have a sensing resistance $R_S$ that is higher than the resistance of the core piece 168 and forward biased resistance of the P-N diode 162.

Figure 17B:
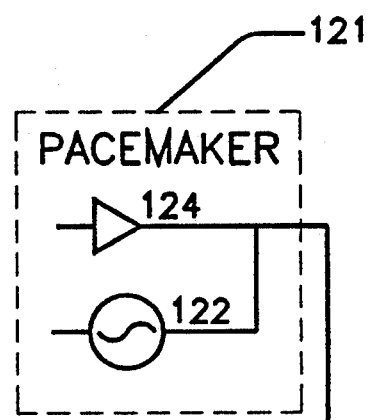
FIG. 17B is a simplified electrical schematic equivalent diagram of the lead tip shown in FIG. 17A.
Figure 17B:
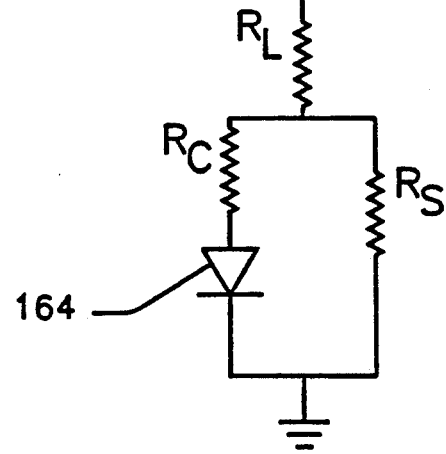

FIG. 17B shows a simplified electrical schematic equivalent diagram of the lead tip 160 shown in FIG. 17A. In FIG. 17B, $R_L$ represents the lead resistance, $R_C$ represents the resistance of the core piece 168, and $R_S$ represents the resistance of the annular sensing electrode 166. The lead tip 160 is connected to a pacemaker 121 that includes a signal generator 122, for generating large amplitude stimulation pulses; and a sense amplifier 124, for sensing low amplitude cardiac signals.

As an example, the sensing electrode 166 may be realized from a semiconductor, e.g., silicon. Silicon advantageously has a negligible impedance relative to the input of the sense amplifier 124. Further, if the electrode 166 needs a better bio-compatible surface or lower polarization surface, it may readily be coated with a special surface e.g. carbon or platinum. The P-N diode 164 may likewise be realized from conventional semiconductor materials, doped as required to provide the desired P-N junction.

In operation, a pacing pulse conducts through the diode 164, and to a much lesser extent (due to the high resistance) through the semiconductor sensing electrode 166. The current associated with the sensing function, i.e., the current induced by cardiac activity, would not conduct at all through the P-N diode 164 since the maximum amplitude will be in tens of millivolts. Note that the diode 164 is in one direction only (for anodic or cathodic pacing). Two parallel diodes, with the anode of one connected to the cathode of the other, could be used for biphasic pacing.

Still referring to FIG. 17A and 17B, it is noted that due to the voltage drop across a forward biased P-N diode, a fair amount of energy may be wasted crossing the diode junction. To gain a benefit from such an electrode construction, the amount of energy conserved by utilizing very small pacing electrodes should be much greater than the amount of energy "wasted" crossing the diode junction. For ventricular applications, a voltage drop of around 50 mv would be close to ideal for the P-N diode 164. Diodes with 0.2–0.3 V forward drop would be just as effective, though less energy efficient.

Fortunately, the breakdown characteristics of most diodes can be manipulated somewhat in terms of breakdown potential and the shape of the voltage-current knee. Such manipulation can be achieved, for example, by utilizing different semiconductors, different dopants, different geometries, etc.

Instead of using a P-N diode 164 in the lead tip, as shown in FIG. 17A, other lead tip constructions may also be employed that offer the same basic advantages as a diode, i.e., voltage-current characteristics that function as a low resistance in one direction, and a high resistance in the other direction, but without some of the disadvantages of a diode, e.g., a forward voltage drop. For example, an electrode may be constructed using a low resistance electrode that is covered with a reconstitutable, low breakdown voltage insulator. At moderately high voltages, the insulative properties of the layer breakdown. Thus, like a diode, current flow rapidly rises. Unlike a diode, there would be little or no voltage drop once current starts to flow. Rather, the conduction becomes almost purely resistive.

The ideal insulator for use with such an alternative construction reconstitutes itself with time to provide its initial properties, or at least properties that are very close to its initial properties. Thus, the next voltage pulse (pacing stimulation pulse) follows essentially the same voltage-current curve.

Typically, once an insulator breaks down, it becomes permanently ineffective. However, this is not so for all insulative layers. For example, a metal conductor insulated by the oxide of the metal would reconstitute itself and have a low breakdown voltage. The metal should be chosen so that its oxide has a very low breakdown ($\approx 50$ mv or less). As long as the electrode is in an oxygen rich environment, the oxide will continually reform. The kinetics required to determine the timing for such metal oxide to reform depends upon the type of metal used.

With the lead designs described above, the sensor electrode area could be enormous. To improve sensor signal amplitude, while having no deleterious effects on pacing, it is noted that the sensing electrode need not to be limited to the pacing tip, but could be located anywhere along the body of the lead.

In its simplest embodiment a pacing lead needs to safely and effectively depolarize excitable tissue. Even in the absence of sensing, it would be an extraordinary advantage to pace using one of the preceding lead constructions.

For unipolar pacing, for example, the E-field in the vicinity of the electrode tip strongly resembles a point source at the center of curvature of the ball tip electrode as depicted previously in FIG. 10B.

If the unexcitable myocardium has a thickness t, it and the E-field must exceed some threshold (say $E_o$) then $$F_o = K q_1 q_2 / (r_o + t)^2. \qquad (2)$$

Thus, the charge ($|Q_1| = |Q_2|$) can be expressed as $$q = k F_o^{\frac{1}{2}} (r_o + t) \qquad (3)$$

or $$q = E_o(r_o + t)^2 \, 4(3.14) e_o. \qquad (4)$$

As an example of the improvement in performance achievable with a lead as described above, i.e., for the case where the pacing electrode may be considered close to a point source, the ratio of charge needed for a depolarization (assuming the same fibrotic response and similar polarization) would be $$\frac{q}{q'} = \frac{E(r+t)^2 k}{Et^2 k} \qquad (5)$$

If $r_o$ is on the order of 1 mm, as is t, then the proposed technique would produce depolarization with $\frac{1}{4}$ the current. Advantageously, if the necrotic zone is diminished or the electric field intensified, the energy savings may be even greater.

It is noted that the energy savings increases dramatically if the fibrotic response is reduced by some means. Suppose, for example, that the thickness of the unexcitable tissue is $\frac{1}{2}$ mm, then the energy used for pacing would be 1/9 that used for a more standard design. In commonly used pacing leads, the electrode size is determined by a compromise among several considerations: fibrotic (immune) response, pacing effectiveness, sensing effectiveness, safety, energy efficiency, etc. Normally, these parameters are unforgivingly interdependent. An electrode which improves sensing, for example, by virtue of increased surface area, may also have a concomitant increase in pacing threshold. Also, since ventricular sensing is relatively trivial and electrodes are "interchangeable" between atria and ventricles, atrial sensing has heretofore been generally poor, occasionally to the point of ineffectiveness.

However, by advantageously designing a lead using the technology disclosed herein, it is possible to design for enhanced sensitivity, particularly relative to atrial sensing. The atrial signal, for example, is relatively low in amplitude and frequency content. Hence, atrial sensing may be difficult. Such sensing may be augmented, however, by increasing the surface area of the sensing electrode. This is particularly true for unipolar pacing where the size of tip sensing electrode may be enlarged to improve the signal amplitude. It should, of course, be noted that the tip (pacing) electrode may not be the best location for the sensing electrode. There are at least 3 reasons for this: (i) the difficulty in sensing at the tip is a direct result of after-polarization associated with the pacing pulse; (ii) the sensing electrode should be proximate the muscle tissue mass where a contraction is to be sensed, i.e., if atrial sensing is desired, the sensing electrode should be proximate to atrial muscle mass; and (iii) the direction of the sensed dipole vector may not be optimized (the cardiac signal relative to the sensing dipole may be improved by a different position of the sensing electrode).

Thus, while atrial pacing may be most reliably performed in the atrial appendage, it may be wise to sense from one or more high impedance sensing electrodes removed from the pacing electrode. Near the SA node is one likely location; mid atrial is another. Since the sensing electrode is designed to have very high impedance, little pacing energy will be wasted through it despite the extremely large exposed surface area; that is, such a construction would advantageously yield higher sensitivity and lower threshold.

One or more high impedance sensing electrodes removed from the pacing electrode is achievable in a single pass lead, described more fully below in connection with FIGS. 19A, 19B and 20. Before describing such a single pass lead, however, it will be helpful to describe how the features associated with the small pacing electrode of the present invention are realized in an active fixation lead tip. This is because active fixation is particularly useful in single pass lead design, although passive fixation single pass leads may also be employed in some instances.

An active fixation lead tip is one wherein some means, such as a helical screw-in tip, is used to actively hold the body tissue against the pacing electrode. Conventional active fixation leads perform well, particularly for stable acute positioning. The large disadvantage of active fixation leads, however is in the quality of the electrode. An unfortunate necessity of conventional active fixation designs is that the electrode must be placed in the immediate vicinity of a considerable local myocardial injury. Such location not only compromises the chronic threshold, but also makes acute positioning difficult due to the effect of the injury on pacing and sensing. Configuring the electrode to a site more removed from the injury would advantageously lower threshold by placing the pacing electrode closer to normal excitable tissue.

Figure 18:
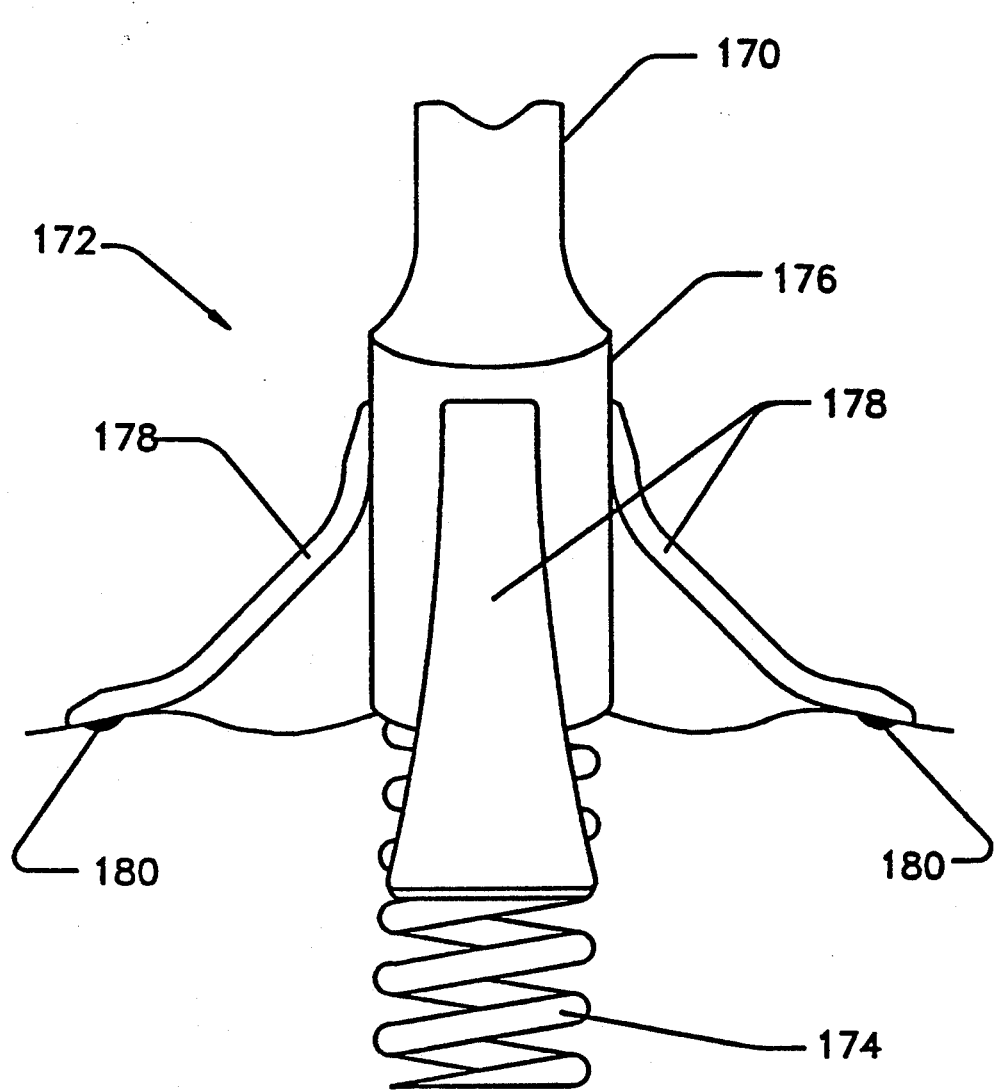
FIG. 18 shows the lead tip of an active fixation lead of the present invention having a plurality of small pacing electrodes embedded in respective polymeric petals at a site removed from the fixation helix.

An exemplary lead 170 having an active fixation tip 172 made in accordance with the present invention is shown in FIG. 18. As seen in FIG. 18, the tip 172 includes a screw-in helix tip 174 that protrudes from an end piece 176. The tip 174 is adapted to be screwed into body tissue 28, in conventional manner. Four petals 176, three of which are visible in FIG. 18, are attached to the end piece 176. On at least one of the petals 176 is included a small pacing electrode 180 positioned so as to be in contact with the body tissue 28 when the tip 174 is secured to the body tissue. Advantageously, the electrode(s) 180 contacts the body tissue 28 at a location removed from the puncture site where the tip 174 screws into the body tissue. The petals 178 are made from a flexible material, such as a suitable polymer. A wire or ribbon conductor is embedded within each of the petals 178 that include an electrode 180. This wire or ribbon conductor electrically connects the electrode 180 to the conductor of the lead 170.

Figure 19A:
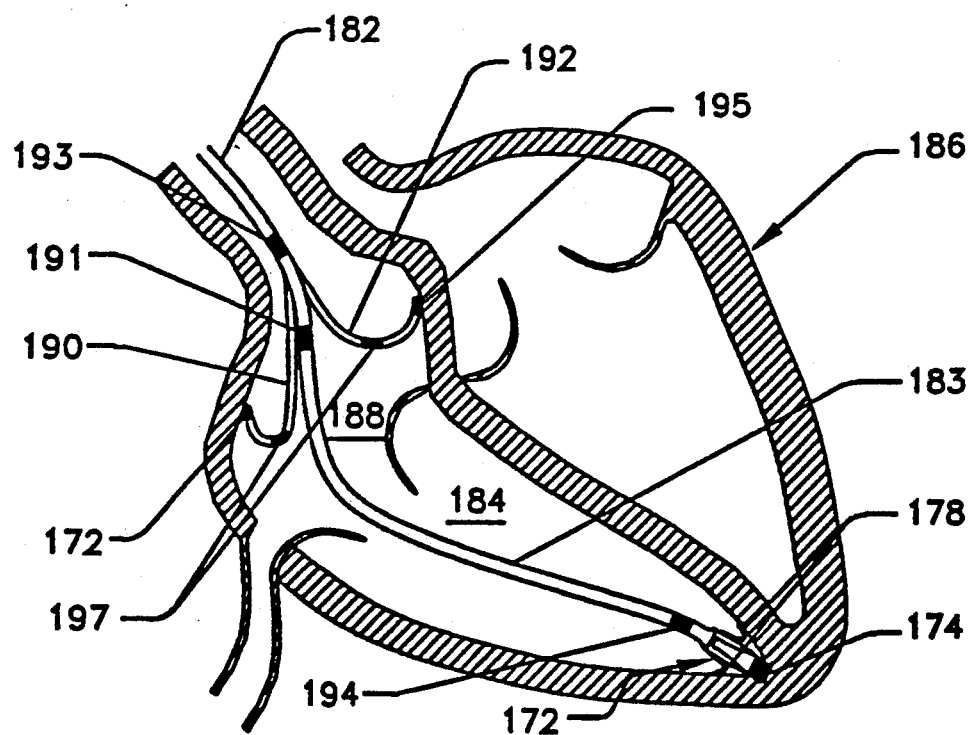
FIGS. 19A and 19B respectively show single pass leads of the present invention having sensing and pacing electrodes positioned in both the atrium and ventricle of a heart.
Figure 19B:
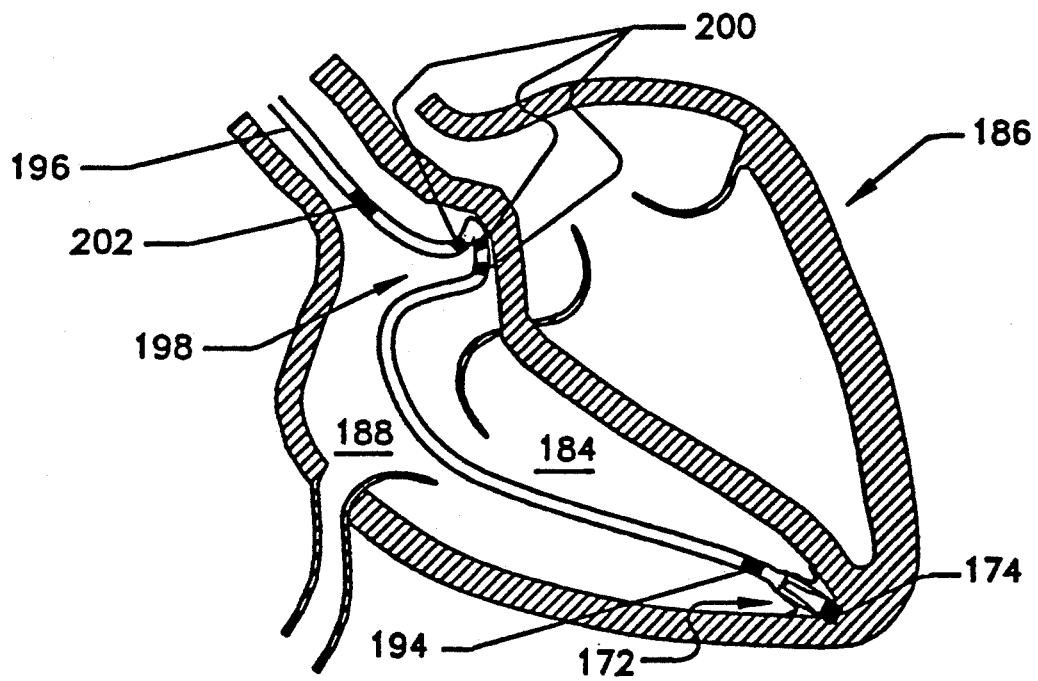
Figure 20:
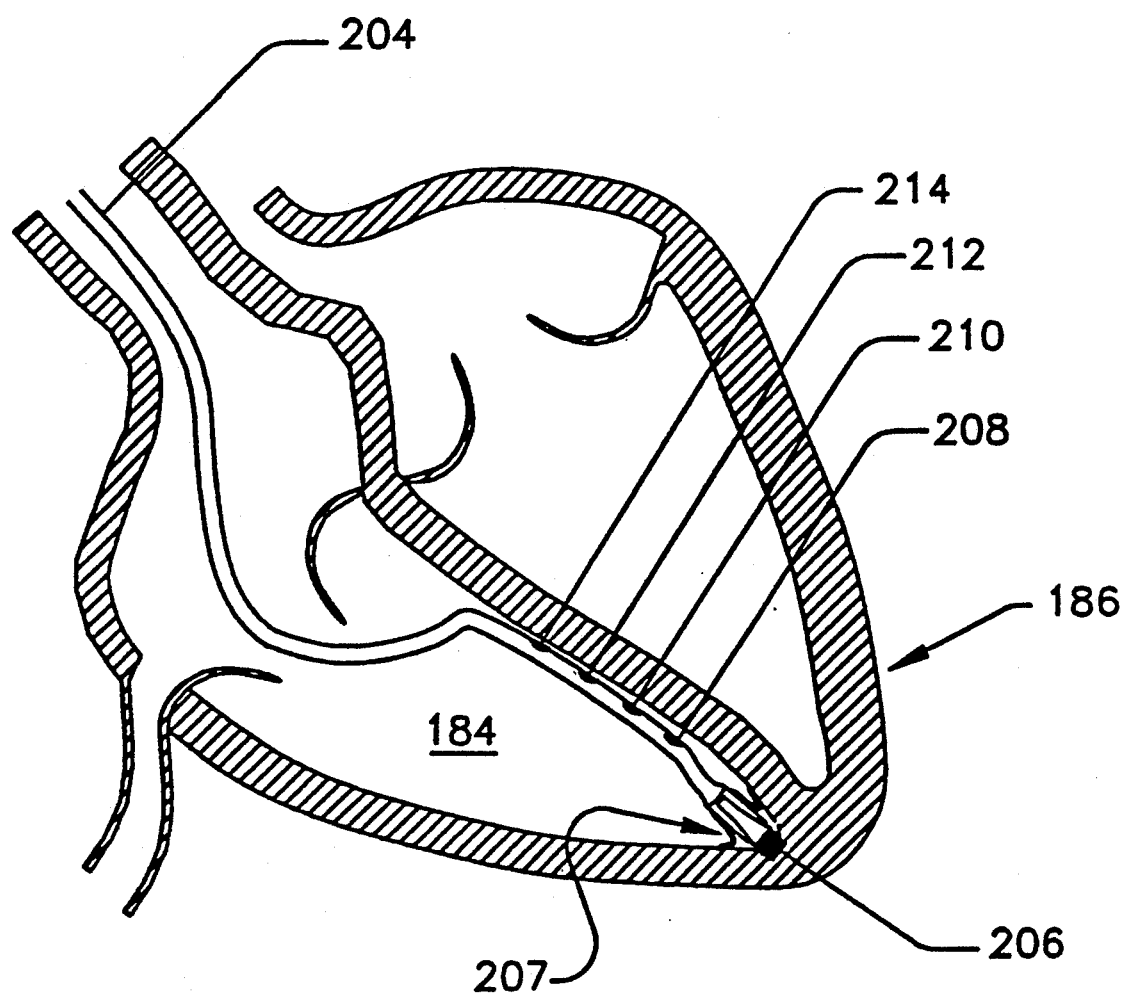
FIG. 20 shows another single pass lead of the present invention having a plurality of electrodes distributed along the body of the lead.

Referring next to FIGS. 19a, 19B and 20, various embodiments of a single pass lead made in accordance with the present invention are illustrated. The aim of a single pass lead, of course, is to provide effective and safe dual chamber pacing and sensing on a single lead which is preferably smaller, less expensive and easier to place than 2 separate leads. Many examples of such leads exist. However, to the inventor's knowledge, none have lived up to their expectations. Generally, the ventricular electrode of a single pass lead is easy to place (much as a standard active-fixation lead). The problem arises when trying, not only to make contact with the atrial endocardium, but to make reliable contact at a spot with low threshold and high sensitivity.

Because of the tremendous variability in cardiac dimensions and excitability (particularly in pacer patients with hypertrophy and/or ischemia) it is very difficult to have a lead design with a single atrial electrode that can make reliable contact in most hearts. Thus, in accordance with the present invention, a multiplicity of atrial electrodes are used so that all are located in the atrium or above and at least one reliably contacts the atrial endocardium.

A first example of such a single pass lead is shown in FIG. 19A, where a single pass lead 182 includes an active fixation tip 172 as described above in FIG. 18 at the end of a ventricular branch 183. The tip 172 is adapted for insertion into the ventricle 184 of a heart 186. Two atrial branches 190 and 192 of the lead 182 split off therefrom in the vicinity of the atrium 188. Each branch is passively deployed within the atrium. The lead body may then be manipulated axially and torsionally to position at least one of the branches to a desired location and then fused in place using conventional fixation means, 195. Thus, once implanted, at least one of the pacing electrodes 197 of the atrial branches 190 and 192 should make good reliable contact with atrial tissue at the same time that the tip 172 of the ventricular branch 183 makes good reliable contact with ventricular tissue. A ventricular sensing electrode 194 of the sort previously described is positioned along the length of the ventricular branch 194. Similarly, atrial sensing electrodes 191 and 193 are positioned, respectively, in the atrium.

Another example of a single pass lead is shown in FIG. 19B. In FIG. 19B, a single pass lead 196 includes an atrial preformed section 198 adapted to loop into the atrial appendage of the right atrium 188. The lead 196 continues into the ventricle 184, where an active fixation tip 172 (as described above in connection with FIG. 18) connects at least one pacing electrode to the ventricular tissue. The atrial preform 198 includes a plurality of small pacing electrodes 200 spaced along its length. At least one of these pacing electrodes should make good contact with the atrial tissue. A ventricular sensing electrode 194 of the sort described above, in the form of a ring electrode, is positioned within the ventricle near the tip 172. An atrial sensing electrode 202, also in the form of a ring electrode, is positioned within the atrium 188, just above the atrial preform 198.

Advantageously, when the atrial pacing electrodes 180 and/or 200 are sufficiently small, each one will only need to use a small amount of energy so that at least one depolarizes the atrium. The sensing electrodes 191, 193, or 202 are attached to the lead in the manner described above. The total energy expended in the atrium is comparable to a conventional atrial lead. The energy expended in pacing the ventricle is much less than in standard ventricular pacing.

For pacemakers that employ auto output adjusting means, where the pacer automatically determines and delivers a pacing pulse that is just slightly greater than the threshold needed to effectuate capture, much energy is already saved by delivering the lowest safe and effective depolarizing pulse. Advantageously, the small electrodes of the present invention further lower the requisite energy.

It is further noted that an auto-adjusting pacer must also include the ability to upwardly adjust its output level. Advantageously, such upward adjustment is made easier by using the pacing leads of the present invention. This is because the electrode depolarizes fewer cells, thereby requiring less energy. Moreover, the small pacing electrode of the present invention is well matched with a low resistance lead when used with an auto adjusting pacer. Thus, pacing voltage is low because of low lead resistance and pacing current is low because of small electrode area.

It is understood that the present invention may incorporate individually addressable electrodes. That is, on a lead with a multitude of electrodes, the electrodes may be independently addressed by a pacer with appropriate programming and connector.

Alternatively, it is noted that such a multiple electrode lead may be tested during implant, as with a PSA (pacing systems analyzer). Each electrode is checked independently. If one electrode is then chosen as best, an adapter may then be placed over the connector so that the one best electrode is selected and paced with any standard pacer.

Advantageously, the above-described electrode-selection capability may be used in many applications. One application, for example, is multiple atrial pacing electrode segment of a single pass lead, as described above in connection with FIG. 19B. Another application is anti-tachycardia pacing. For effective anti-tachycardia pacing it is desirable to have an array of electrodes, both for sensing and pacing. Regardless of whether the construction is as a standard lead or one with multiple independently addressable electrodes or even an epicardial net of electrodes, it is good to have high sensitivity and low pacing thresholds. This is especially true if pacing is done at several sites or several times in a given pacing cycle, where energy usage is more critical. A versatile construction allows different electrodes to be addressed without the need for invasiveness to change the connections.

The use of a multiplicity of electrodes in a single chamber of the heart can provide more physiologic pacing in those patients with ischemia blocking normal conduction or disease of the specialized conduction system within the myocardium—the His/Perkinje system within the ventricular myocardium. In such patients it is possible to perform single chamber sequential pacing. In healthy hearts, increased cardiac output is met by faster rate and/or increased stroke volume. The rate of ventricular wall motion increases, as do pressure and dP/dt (the rate of change of pressure with respect to time). Even in rate responsive pacer patients, cardiac output can only be controlled by varying pacer rate. However, by using a lead as described herein that is able to pace multiple sites in the heart, it is possible to enhance emptying of the heart chamber (by squeezing the blood out of the ventricles in a more physiologic manner). Not only can cardiac output be increased during exercise by using such a multiple site pacing lead, such lead also permits the heart to pump more efficiently and effectively at rest (during non-exercise periods). This is especially true in hearts exhibiting broad QRS complexes, in which conduction is not normally through the His/Perkinje system.

In order to effectively pace at multiple sites in a single chamber, the ventricular apex is paced first with the remaining electrodes distributed in a logically synchronous order so that a fast moving contractile wave is created. An exemplary model of such a lead is shown in FIG. 20. As seen in FIG. 20, a pacing lead 204 includes fixation means 206 for holding the distal tip 207 of the lead at a desired location near the apex of the ventricle. While active fixation means are shown in FIG. 20 (an active fixation screw-in tip), it is to be understood that passive fixation means could also be used. A first small pacing electrode 208 is positioned near the distal tip 207. Other small pacing electrodes 210, 212, and 214 are spaced along the length of the lead 204 within the ventricle 184. If necessary, the lead 204, or equivalents thereof, may be placed epicardially so that the left ventricle may also be paced.

While the delay between application of pacing pulses at the respective pacing electrodes 208, 210, 212, and 214 may be imposed by the pacer, such would require extra hardware, software, insulated conductors, etc. A simpler approach is to build an electrical delay into the lead. One way this may be done is via LC connections or networks built within the lead (inductive delay). By building delays into the lead, a standard pacing connector may be used. The pacing impulse would thus travel directly to the distal electrode 208 then in sequence travel to each successive electrode 210, 212, and 214.

Applications for a lead such as is shown in FIG. 20, or equivalents thereof, would be in patients who need augmented ejection fraction, such as those with bundle branch block or widespread ischemia. Pacing for such patients may be atrial or ventricular though ventricular is likely to be much more effective. The pacer used with such a lead may be standard or a special closed loop stroke volume adjusting pacer. Ultimately, cardiac output is controlled by the pacer by adjusting stroke volume and rate in concert with the patient's intrinsic responses.

As described above, it is thus seen that the present invention provides a construction for a cardiac pacing lead that provides a lower pacing threshold than is achieved with conventional pacing leads. Advantageously, such improved pacing function is provided with no degradation of the sensing function of the lead, and in fact with an enhanced sensing function for many embodiments.

As also seen from the above description, the present invention achieves its goals of improved sensing and pacing function without the need for specialized pacers or connectors.

As further seen from the preceding description, the present invention achieves low pacing thresholds and high sensitivity in active fixation leads.

Still further, it is seen that the invention provides, in one embodiment thereof, a pacing lead having multiple pacing electrode capability, in addition to the sensing capability. Such multiplicity of pacing electrodes advantageously provides additional pacing capability and pacing options within a given chamber of the heart.

What is claimed is:

1. A cardiac pacing lead comprising:
   a conductive lead body;
   an insulative sheath covering said conductive lead body;
   means for connecting the lead body to a pacemaker at a proximal end of the lead body;
   a pacing electrode for making physical contact with myocardial tissue at or near a distal end of the lead body, said physical contact having a lead force associated therewith;
   a sensing electrode adapted to sense cardiac activity, said sensing electrode being electrically connected to the pacing electrode, said sensing electrode having an electrical resistance that is at least twice that of the pacing electrode; and
   mechanical means located at or near the distal tip of the lead body for distributing a portion of the lead force to an area of the myocardial tissue spaced apart from the pacing electrode.

2. The cardiac pacing lead as set forth in claim 1 wherein the pacing electrode is located near the distal tip of the lead, and wherein the pacing lead includes separate means apart from said pacing electrode for holding the pacing electrode on the surface of the heart.

3. The cardiac pacing lead as set forth in claim 1 further including means for concentrating the electrical energy available at the pacing electrode in the myocardium of a heart wherein the pacing lead is inserted.

4. The cardiac pacing lead as set forth in claim 1 wherein the electrical connection between the pacing electrode and the sensing electrode has an electrical resistance that is at least twice the resistance of the pacing electrode.

5. The cardiac pacing lead as set forth in claim 4 wherein the electrical connection between the pacing electrode and the sensing electrode is made through a resistor.

6. A cardiac pacing lead comprising:
   a conductive lead body for conducting electrical impulses;
   an insulative sheath for covering said lead body;
   means for electrically and mechanically connecting the lead body to a pacemaker at a proximal end of the lead body;
   a plurality of pacing electrodes, each having a resistivity associated therewith, for making physical contact with myocardial tissue at or near a distal tip of the lead body, said physical contact having a lead force associated therewith; and
   mechanical means located at the distal tip of the lead body for distributing a portion of the lead force to an area of the heart disposed away from the pacing electrodes, said mechanical means including a material having a resistivity at least ten times higher than the resistivity of the pacing electrode.

7. The cardiac pacing lead as set forth in claim 6 wherein the pacing electrodes are contained within the boundaries of the mechanical means.

8. The cardiac pacing lead as set forth in claim 7 further including a sensing electrode in electrical contact with said conductive lead body.

9. An implantable lead for use with a stimulation device comprising:
   a flexible conductor having proximal and distal ends;
   an elongate insulating sheath surrounding said flexible conductor,
   a pacing electrode at the distal end of said flexible conductor, said pacing electrode being in electrical contact with said flexible conductor and having a surface area that is less than approximately 5 mm$^2$,
   means at the proximal end of said flexible conductor for making electrical contact with said stimulation device,
   means for positioning the pacing electrode offline from a longitudinal axis of said implantable lead, and
   force-distribution means at the distal end of said flexible conductor for distributing the longitudinal holding forces associated with holding the distal end of said lead against cardiac tissue over a tissue area that is at least four times as large as the surface area of said pacing electrode.

10. The implantable lead as set forth in claim 9 wherein said force-distribution means comprise a paraboloid-shaped head at the distal end of said lead.

11. The implantable lead as set forth in claim 9 wherein said force-distribution means comprise a said lead, said pacing electrode being positioned near an edge of said umbrella-shaped head.

12. An implantable lead for use with a stimulation device comprising:
   a flexible conductor having proximal and distal ends;
   an elongate insulating sheath surrounding said flexible conductor,
   a pacing electrode at the distal end of said flexible conductor, said pacing electrode being in electrical contact with said flexible conductor through a pacing impedance and having a surface area that is less than approximately 5 mm$^2$,
   means at the proximal end of said flexible conductor for making electrical contact with said stimulation device, and
   a sensing electrode proximal the distal end of said flexible conductor, said sensing electrode being in electrical contact with said flexible conductor through a sensing impedance, said sensing electrode having a surface area that is at least 2 times the surface area of said pacing electrode; whereby said sensing electrode and sensing impedance present a sensing circuit impedance, said sensing circuit impedance presenting a circuit resistance greater than approximately 10,000 ohms, and said pacing impedance presenting a circuit resistance less than approximately 1,000 ohms, whereby most of the pacing current flows through said pacing electrode.

* * * * *